(12) United States Patent
Inoue

(10) Patent No.: US 11,786,387 B2
(45) Date of Patent: Oct. 17, 2023

(54) STENT GRAFT TRANSPORT DEVICE

(71) Applicant: PTMC Institute, Kyoto (JP)

(72) Inventor: Kanji Inoue, Kyoto (JP)

(73) Assignee: PTMC INSTITUTE, Kyoto (JP)

( * ) Notice: Subject to any disclaimer, the term of this patent is extended or adjusted under 35 U.S.C. 154(b) by 393 days.

(21) Appl. No.: 16/765,996

(22) PCT Filed: Nov. 26, 2018

(86) PCT No.: PCT/JP2018/043454
§ 371 (c)(1),
(2) Date: May 21, 2020

(87) PCT Pub. No.: WO2019/103148
PCT Pub. Date: May 31, 2019

(65) Prior Publication Data
US 2020/0352757 A1    Nov. 12, 2020

(30) Foreign Application Priority Data
Nov. 24, 2017    (JP) .................................. 2017-225807

(51) Int. Cl.
*A61F 2/92* (2013.01)
*A61F 2/954* (2013.01)
(Continued)

(52) U.S. Cl.
CPC ................ *A61F 2/954* (2013.01); *A61F 2/07* (2013.01); *A61F 2/9522* (2020.05);
(Continued)

(58) Field of Classification Search
CPC .......... A61F 2/954; A61F 2/9522; A61F 2/07; A61F 2/95; A61F 2/962; A61F 2/966;
(Continued)

(56) References Cited

U.S. PATENT DOCUMENTS

| 6,537,284 | B1 | 3/2003 | Inoue | |
| 2005/0090890 | A1* | 4/2005 | Wu | A61M 25/0021 |
| | | | | 606/108 |

(Continued)

FOREIGN PATENT DOCUMENTS

| CN | 101045022 A | 10/2007 |
| CN | 104042379 A | 9/2014 |

(Continued)

OTHER PUBLICATIONS

China National Intellectual Property Administration, Office Action and Search Report Issued in Application No. 201880073048.1, dated Oct. 11, 2021, 19 pages.

(Continued)

*Primary Examiner* — Erich G Herbermann
(74) *Attorney, Agent, or Firm* — Alleman Hall Creasman & Tuttle LLP

(57) ABSTRACT

A stent graft transport device includes a mounted state keeping wire that keeps a mounted state of a stent graft on a transport tube or a contracted state keeping wire that keeps a contracted state of the stent graft. The transport tube can be separated from the stent graft by pulling an operation end part of the mounted state keeping wire, and the stent graft can be in an expanded state by pulling an operation end part of the contracted state keeping wire. Furthermore, the operation end part of each of the wires is housed inside the transport tube. In order to draw the operation end part, a wire pulling-out string is provided, one end part of which is mounted on the mounted state keeping wire and the other end part of which is pulled out from a window arranged on a side peripheral surface of the transport tube.

10 Claims, 28 Drawing Sheets

(51) Int. Cl.
  *A61F 2/95* (2013.01)
  *A61F 2/07* (2013.01)
  *A61F 2/06* (2013.01)
(52) U.S. Cl.
  CPC .............. *A61F 2002/061* (2013.01); *A61F 2002/9534* (2013.01); *A61F 2210/0014* (2013.01); *A61F 2250/0067* (2013.01)
(58) Field of Classification Search
  CPC .......... A61F 2/013; A61F 2/01; A61F 2/2427; A61F 2/2418; A61F 2002/061; A61F 2002/9534; A61F 2210/0014; A61F 2250/0067; A61M 25/0147
  See application file for complete search history.

(56) References Cited

U.S. PATENT DOCUMENTS

| | | | | |
|---|---|---|---|---|
| 2008/0109058 | A1* | 5/2008 | Greenberg | A61F 2/95 623/1.13 |
| 2009/0099640 | A1* | 4/2009 | Weng | A61F 2/95 623/1.11 |
| 2012/0172965 | A1 | 7/2012 | Kratzberg et al. | |
| 2013/0123900 | A1* | 5/2013 | Eblacas | A61F 2/95 623/1.13 |
| 2015/0216694 | A1 | 8/2015 | Ducke et al. | |
| 2017/0007391 | A1 | 1/2017 | Inoue | |

FOREIGN PATENT DOCUMENTS

| | | |
|---|---|---|
| JP | H04322665 A | 11/1992 |
| JP | J2000000312 A | 1/2000 |
| JP | 2004329955 A | 11/2004 |
| JP | 2011516202 A | 5/2011 |
| JP | 2011522590 A | 8/2011 |
| JP | 2012139500 A | 7/2012 |
| JP | 2015514548 A | 5/2015 |
| WO | 0025847 A1 | 5/2000 |

OTHER PUBLICATIONS

ISA Japan Patent Office, International Search Report Issued in International Application No. PCT/JP2018/043454, dated Jan. 22, 2019, WIPO, 4 pages.

* cited by examiner

STENT GRAFT TRANSPORT DEVICE

TECHNICAL FIELD

This invention relates to an artificial blood vessel transport device that transports and indwells an artificial blood vessel such as a stent graft to a desired position.

BACKGROUND ART

Recently, as shown in the patent document 1, a stent graft comprising a main tube and a branch tube that branches from the main tube has been developed.

The stent graft having the branch tube is to be transported to and indwelled in, for example, the arch aorta and a bifurcated blood vessel (for example, the left subclavian artery) that bifurcates from the arch aorta.

A process of transporting and indwelling the branched stent graft (especially a process of indwelling the branch tube) will be explained specifically.

The main tube is folded in a long and thin state (a contracted state) and mounted on a circumference of a first transport tube inside of which a guide wire passes. In addition, the branch tube is also folded in a long and thin state (a contracted state) and placed along the main tube, and the branched stent graft is maintained in a long and thin state overall.

The above-mentioned branched stent graft is housed in a sheath catheter beforehand in a long and thin folded state. With this state kept, the sheath catheter is inserted into the blood vessel. When the sheath catheter reaches the ventral aorta or the thoracic aorta, the branched stent graft housed inside of the sheath catheter is pushed into the inside of the blood vessel from the sheath catheter by the use of a first transport tube and then is transported to a bifurcated position along a guide wire.

With this procedure, the main tube is transported to a desired position, and it is necessary to insert the branch tube into the bifurcated blood vessel.

Then, a second transport tube is mounted on a distal end part of the branch tube to extend therefrom, and a distal end part of the second transport tube is pulled out by an operator while grasping a holding wire that is inserted from a distal end side of the bifurcated blood vessel. With this procedure, the second transport tube is inserted into the bifurcated blood vessel and the branch tube is introduced into the bifurcated blood vessel accordingly. In this state, the distal end part of the second transport tube is pulled out to the outside of a body from the distal end side of the bifurcated blood vessel.

Meanwhile, a contracted state keeping wire to keep the branch tube in a folded state (a contracted state) and a mounted state keeping wire to keep the branch tube in a mounted state of the branch tube on the second transport tube are housed in the second transport tube.

After the operator introduces the branch tube into the bifurcated blood vessel with the above-mentioned procedure, the operator pulls and draws out the contracted state keeping wire from the distal end part of the second transport tube that is pulled out to the outside of the body. With this procedure, the contracted state of the branch tube is released and expanded. Then, similar to this process, the operator pulls and draws out the mounted state keeping wire from the distal end part of the second transport tube. With this procedure, the mounted state of the branch tube is released. Then, the operator removes the second transport tube from the branch tube. Finally, the operator pulls out the second transport tube to the outside of the body and indwells the branch tube to the inside of the bifurcated blood vessel.

CITATION LIST

Patent Literature

Patent document 1: Domestic Republication of PCT International Publication No. 00/025847

SUMMARY OF INVENTION

Technical Problem

In the above-mentioned process, however, a task of pulling and drawing out the contracted state keeping wire and the mounted state keeping wire from the distal end part of the second transport tube is complicated.

For example, a window is provided on an outer peripheral surface of the second transport tube, the contracted state keeping wire and the mounted state keeping wire are exposed through the window, and the contracted state keeping wire and the mounted state keeping wire are picked up and drawn out through the window by an operator with tweezers or the like. With this arrangement, there is a possibility that it might take time for the operator to pick up and draw out the contracted state keeping wire and the mounted state keeping wire or the operator might cut the contracted state keeping wire and the mounted state keeping wire in the process of picking them up and eventually it might take further time. This problem is common to not only the branch tube, but also a stent graft having a similar transport arrangement.

The present claimed invention aims to solve the above-mentioned problem, and to facilitate an operation of releasing the mounted state of the stent graft on the transport tube or an operation of releasing the contracted state of the stent graft by making it possible to simply and securely pull out the mounted state keeping wire that keeps the mounted state of the stent graft on the transport tube or the contracted state keeping wire that keeps the contracted state of the stent graft.

Solution to Problem

More specifically, a stent graft transport device in accordance with this invention is a stent graft transport device that comprises a transport tube to transport a stent graft and a mounting mechanism to mount the stent graft on the transport tube, and is so configured that the mounting mechanism comprises a mounted state keeping wire that keeps a mounted state of the stent graft on the transport tube, and the transport tube can be separated from the stent graft by releasing the mounted state with an operation of pulling an operation end part of the mounted state keeping wire, and is characterized by that the operation end part of the mounted state keeping wire is housed inside of the transport tube, and a mounted state keeping wire pulling-out mechanism to draw the operation end part out of the transport tube includes a mounted state keeping wire pulling-out string, one end part of which is mounted on the mounted state keeping wire and the other end part of which is pulled out from a mounted state keeping wire pulling-out window arranged on a side peripheral surface of the transport tube.

In addition, a stent graft transport device in accordance with this invention is a stent graft transport device that comprises a transport tube to transport a stent graft and a contraction mechanism to contract the stent graft, and is so configured that the contraction mechanism comprises a contracted state keeping wire that keeps a contracted state of the stent graft, and the stent graft can be in an expanded state by releasing the contracted state of the stent graft with an operation of pulling an operation end part of the contracted state keeping wire, and is characterized in that the operation end part of the contracted state keeping wire is housed inside of the transport tube, and a contracted state keeping wire pulling-out mechanism to draw the operation end part out of the transport tube comprises a contracted state keeping wire pulling-out string, one end part of which is mounted on the contracted state keeping wire and the other end part of which is pulled out from a contracted state keeping wire pulling-out window arranged on a side peripheral surface of the transport tube.

Advantageous Effects of the Invention

In accordance with this invention, it becomes possible to simply and securely dismount the transport tube from the stent graft after the stent graft is indwelled in a predetermined portion of the blood vessel, or to expand the contracted stent graft at a time of indwelling the stent graft.

Figure 13:
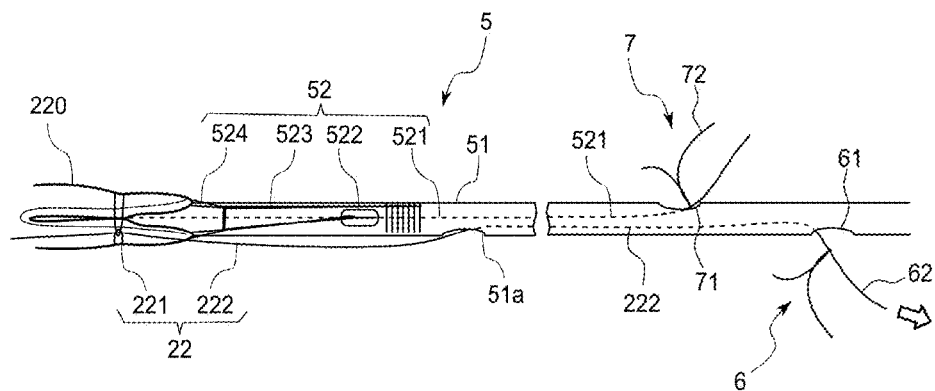

FIG. 13 is a process explanatory view showing a process of expanding a branch tube in a contracted state by making use of the second expansion mechanism and the control wire pulling-out mechanism and a following process of separating the branch tube from the second transport tube by making use of the second mounting mechanism and the engaging wire pulling-out mechanism in accordance with the first embodiment.

Figure 14:
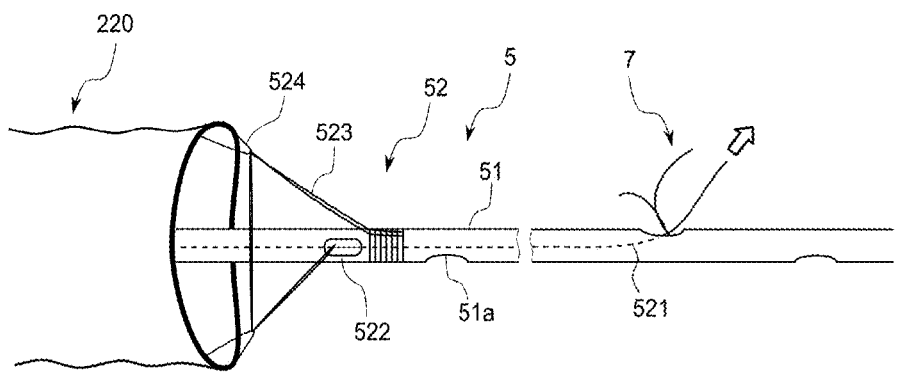

FIG. 14 is a process explanatory view showing a process of expanding the branch tube in the contracted state by making use of the second expansion mechanism and the control wire pulling-out mechanism and a following process of separating the branch tube from the second transport tube by making use of the second mounting mechanism and the engaging wire pulling-out mechanism in accordance with the first embodiment.

Figure 15:
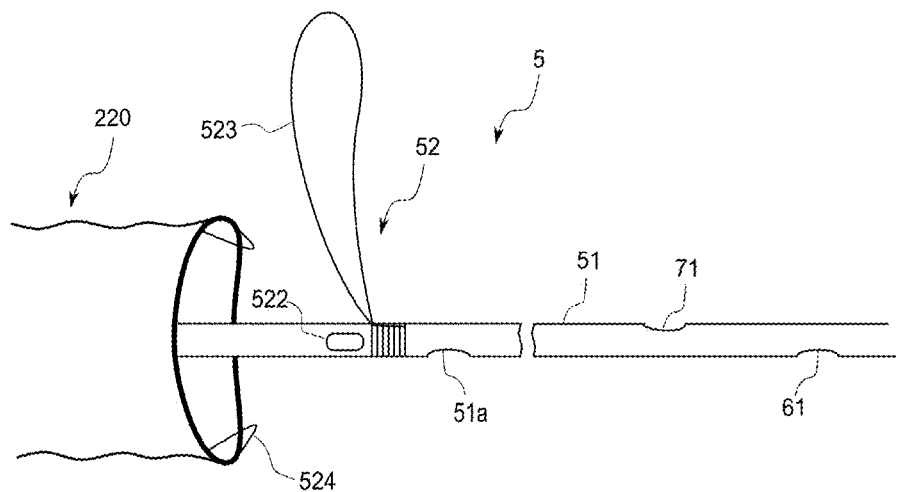

FIG. 15 is a process explanatory view showing a process of expanding the branch tube in the contracted state by making use of the second expansion mechanism and the control wire pulling-out mechanism and a following process of separating the branch tube from the second transport tube by making use of the second mounting mechanism and the engaging wire pulling-out mechanism in accordance with the first embodiment.

Figure 16:
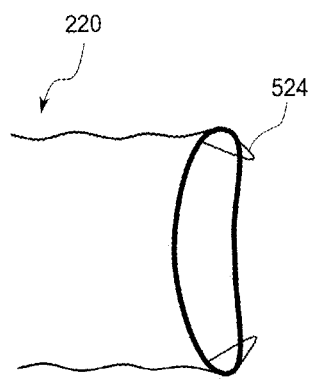

FIG. 16 is a process explanatory view showing a process of expanding the branch tube in the contracted state by making use of the second expansion mechanism and the control wire pulling-out mechanism and a following process of separating the branch tube from the second transport tube by making use of the second mounting mechanism and the engaging wire pulling-out mechanism in accordance with the first embodiment.

Figure 17:
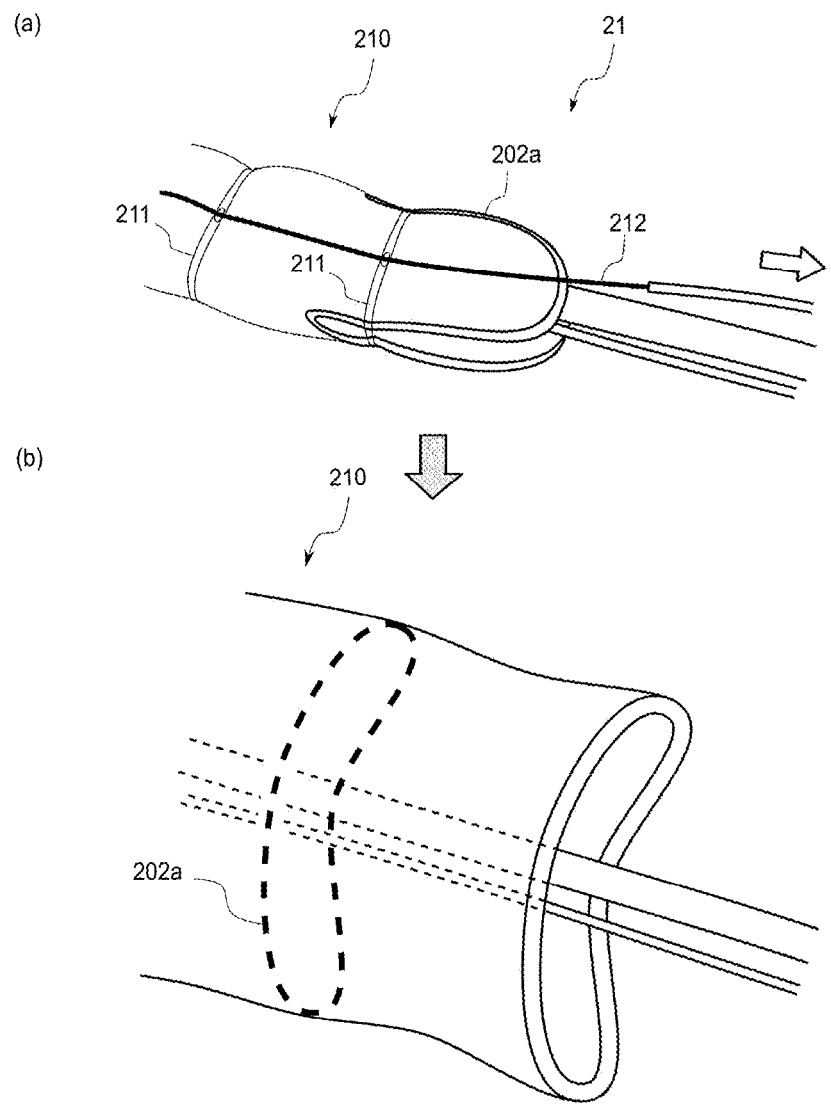

FIG. 17 is a process explanatory view showing a process of expanding the main tube in the contracted state by making use of the first expansion mechanism in accordance with the first embodiment.

Figure 18:
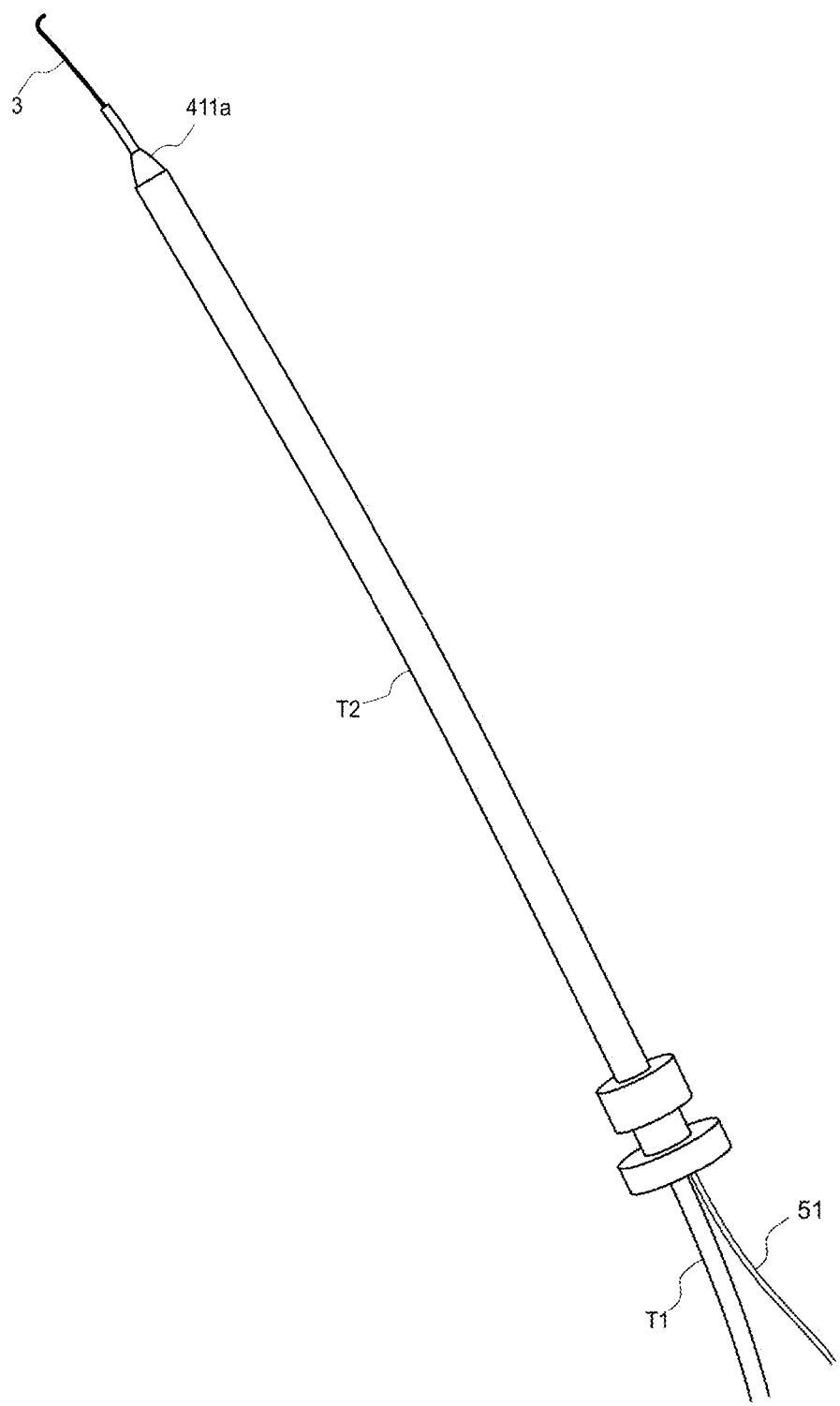

FIG. 18 is a process explanatory view showing a process of indwelling the stent graft in the inside of the blood vessel by making use of the stent graft transport device in accordance with the first embodiment.

Figure 19:
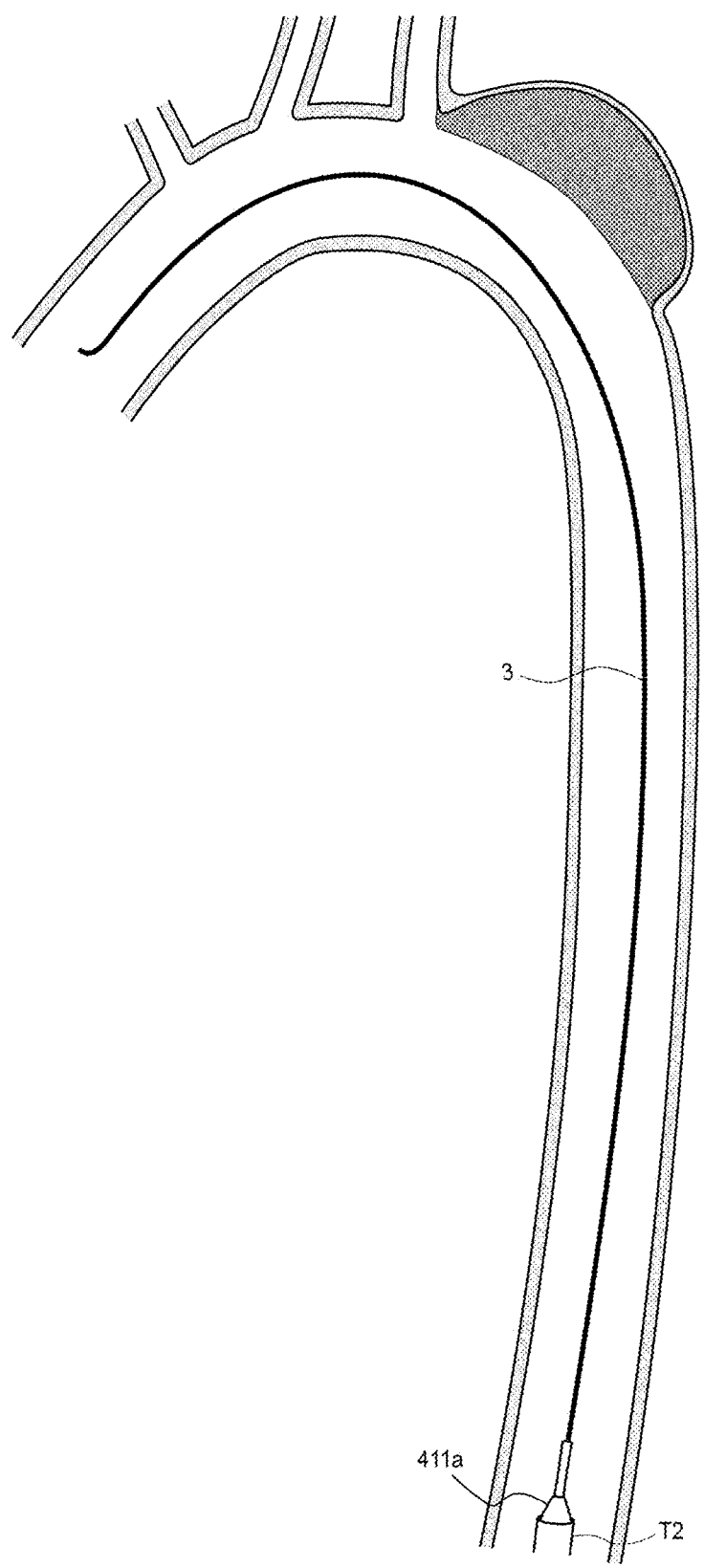

FIG. 19 is a process explanatory view showing a process of indwelling the stent graft in the inside of the blood vessel by making use of the stent graft transport device in accordance with the first embodiment.

Figure 20:
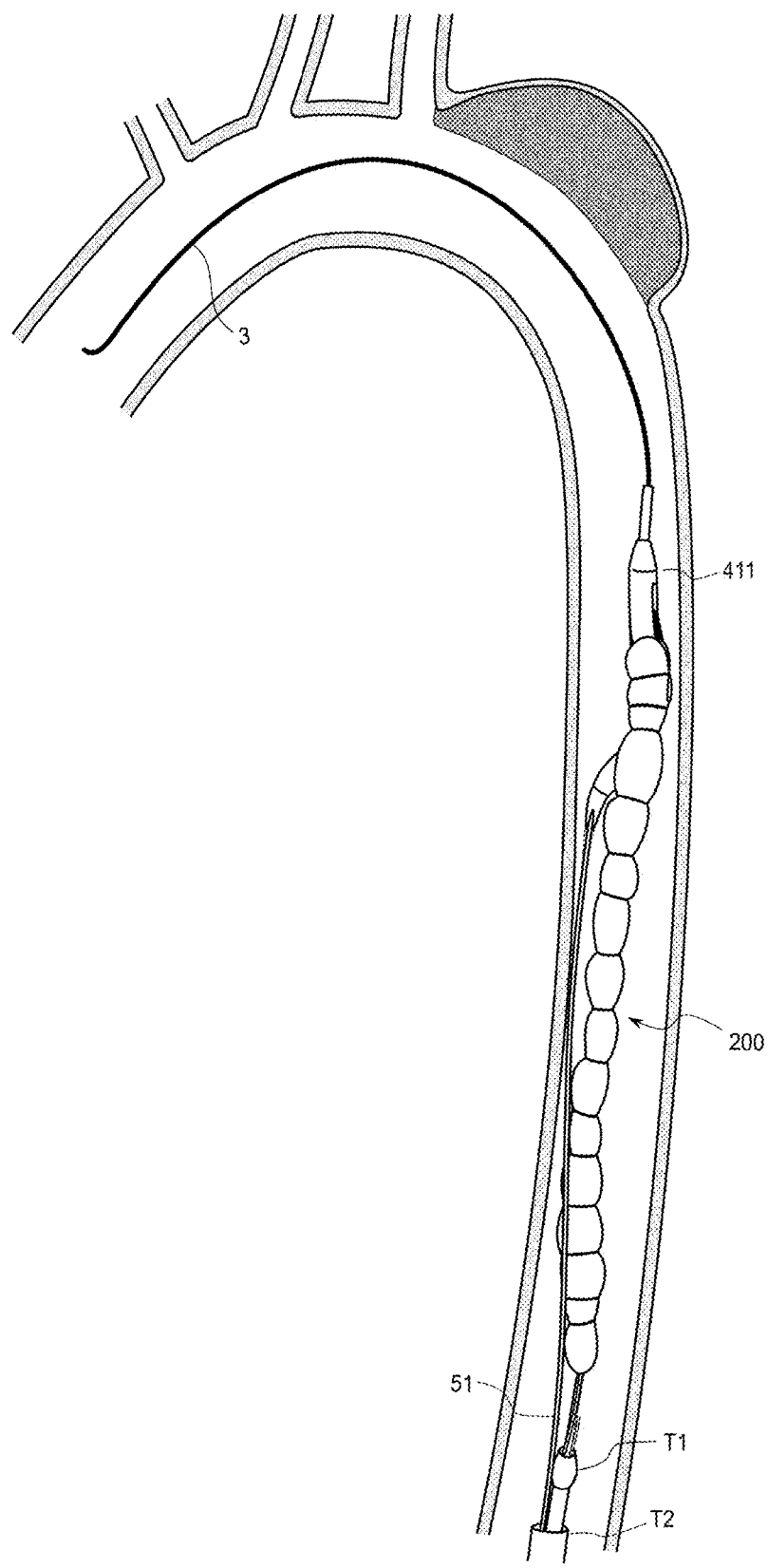

FIG. 20 is a process explanatory view showing a process of indwelling the stent graft in the inside of the blood vessel by making use of the stent graft transport device in accordance with the first embodiment.

Figure 21:
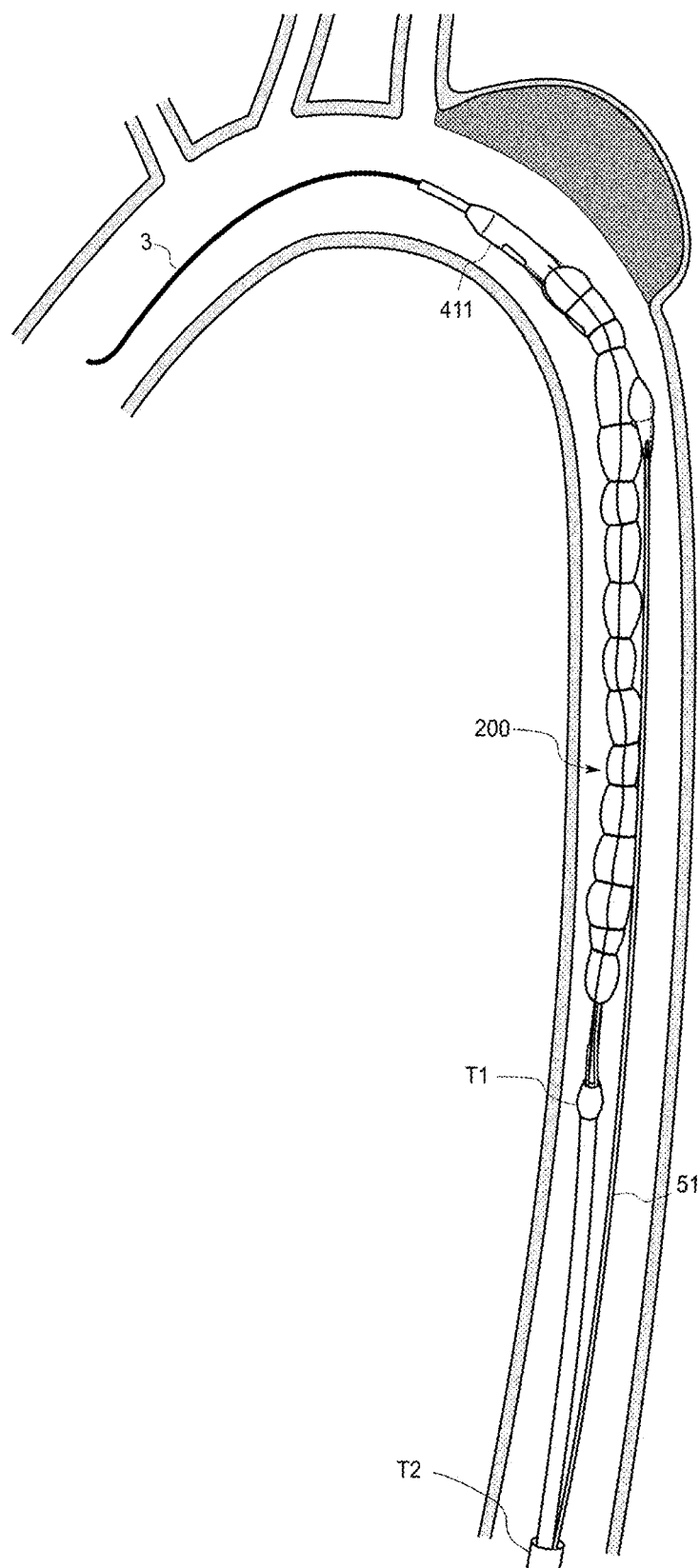

FIG. 21 is a process explanatory view showing a process of indwelling the stent graft in the inside of the blood vessel by making use of the stent graft transport device in accordance with the first embodiment.

Figure 22:
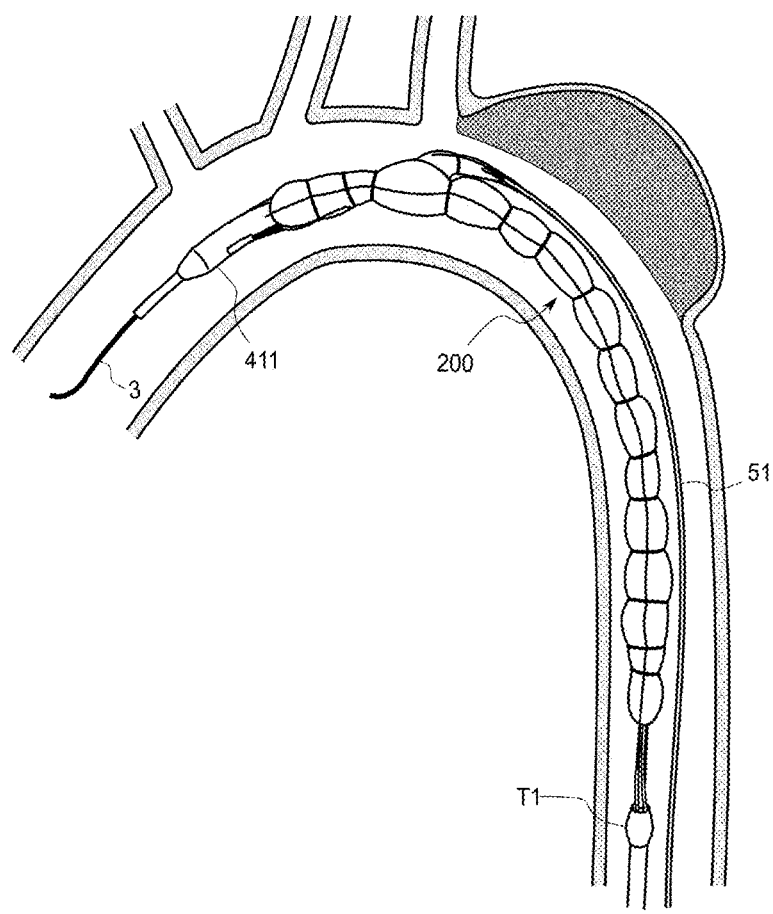

FIG. 22 is a process explanatory view showing a process of indwelling the stent graft in the inside of the blood vessel by making use of the stent graft transport device in accordance with the first embodiment.

Figure 23:
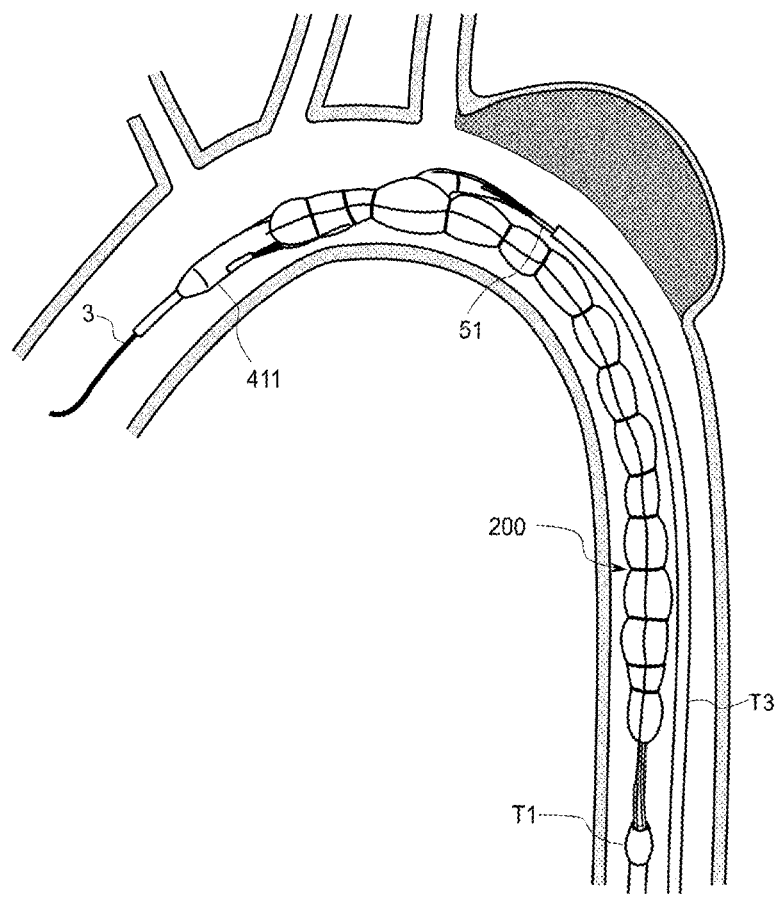

FIG. 23 is a process explanatory view showing a process of indwelling the stent graft in the inside of the blood vessel by making use of the stent graft transport device in accordance with the first embodiment.

Figure 24:
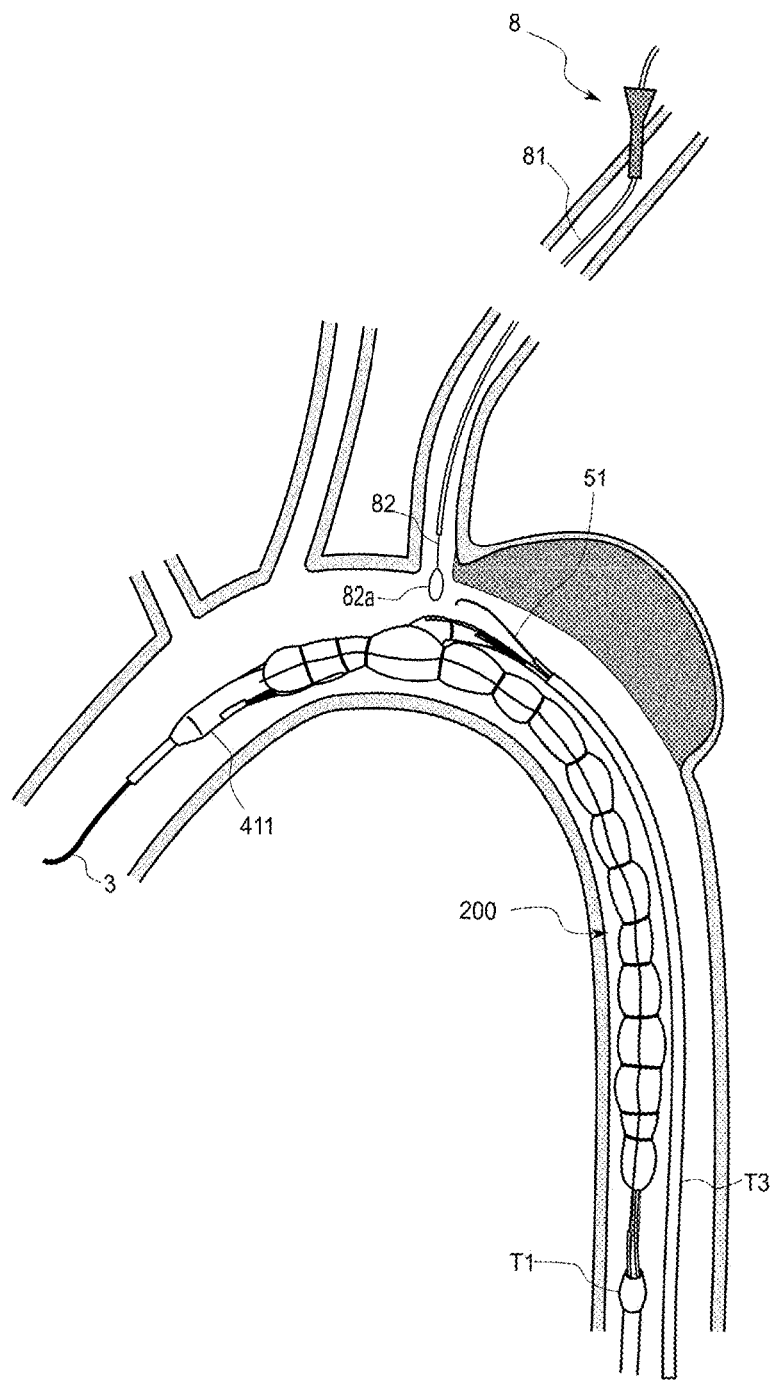

FIG. 24 is a process explanatory view showing a process of indwelling the stent graft in the inside of the blood vessel by making use of the stent graft transport device in accordance with the first embodiment.

Figure 25:
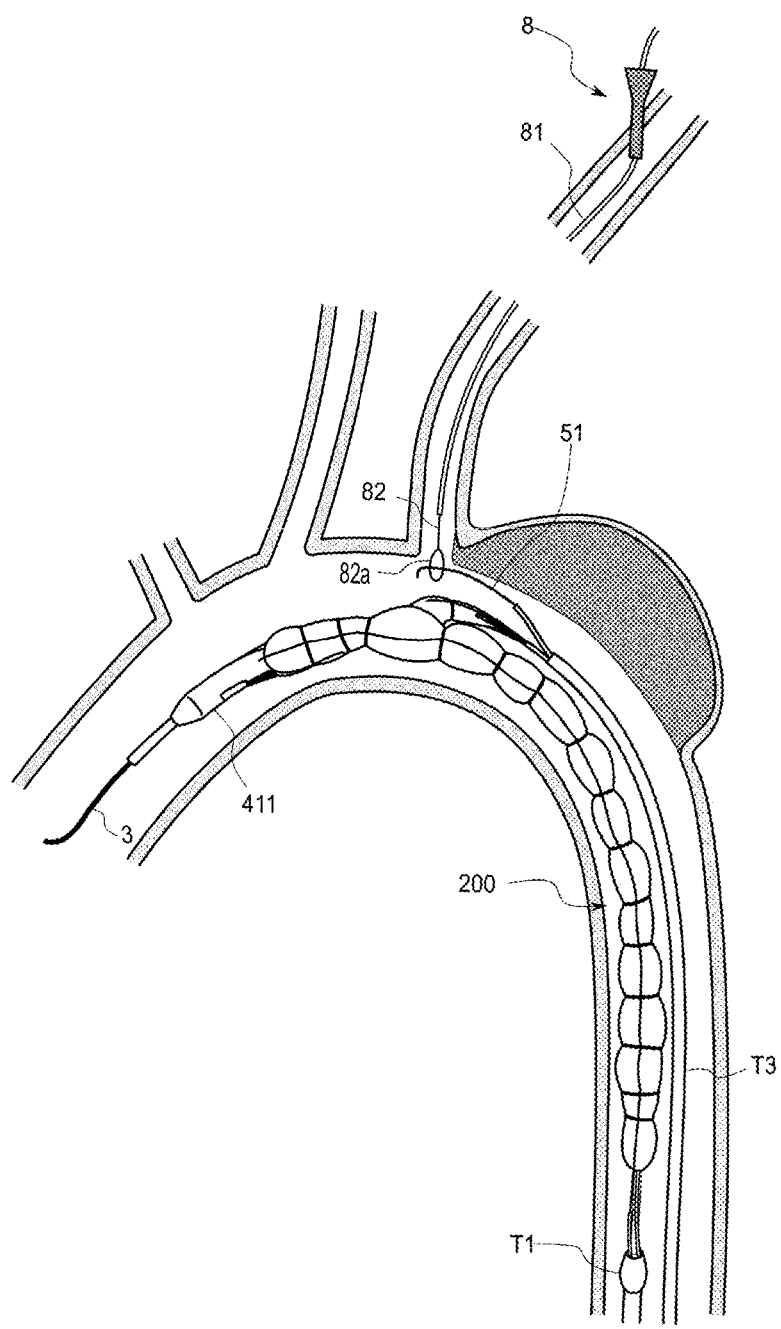

FIG. 25 is a process explanatory view showing a process of indwelling the stent graft in the inside of the blood vessel by making use of the stent graft transport device in accordance with the first embodiment.

Figure 26:
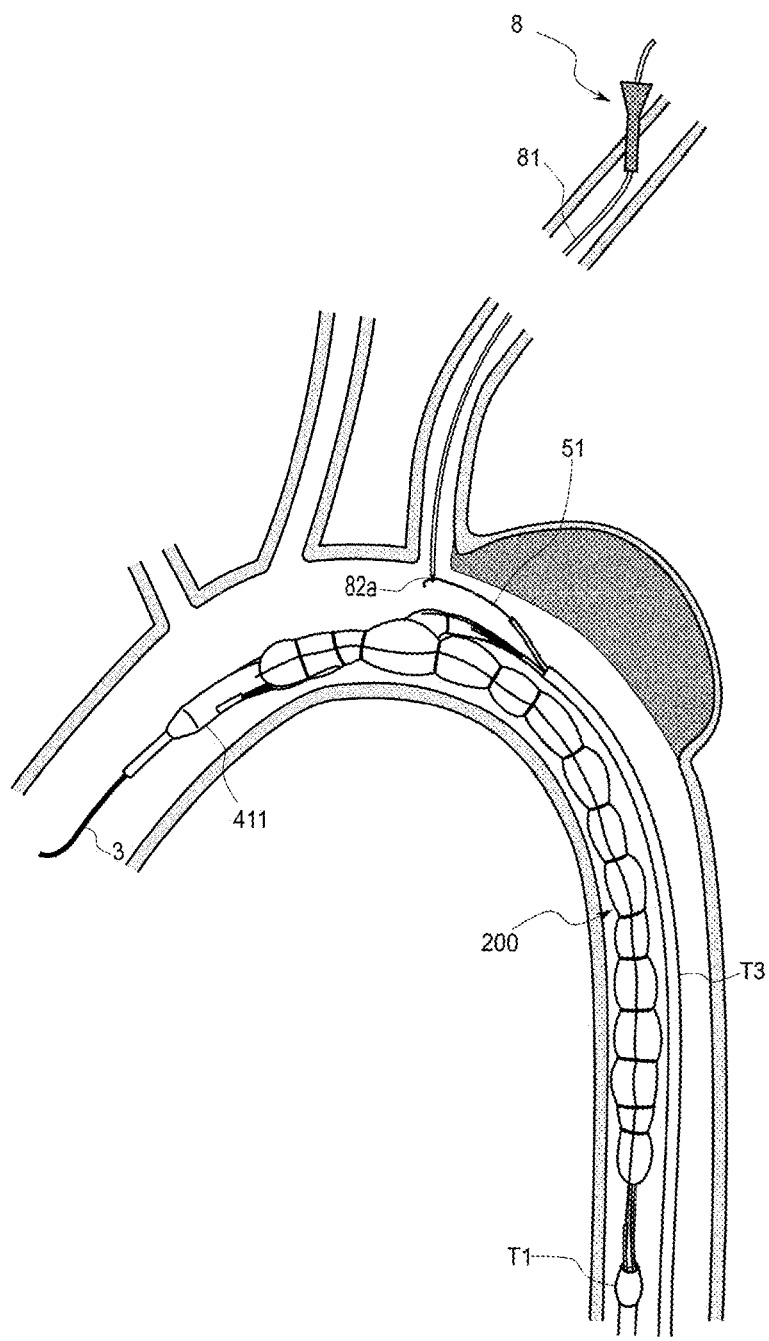

FIG. 26 is a process explanatory view showing a process of indwelling the stent graft in the inside of the blood vessel by making use of the stent graft transport device in accordance with the first embodiment.

Figure 27:
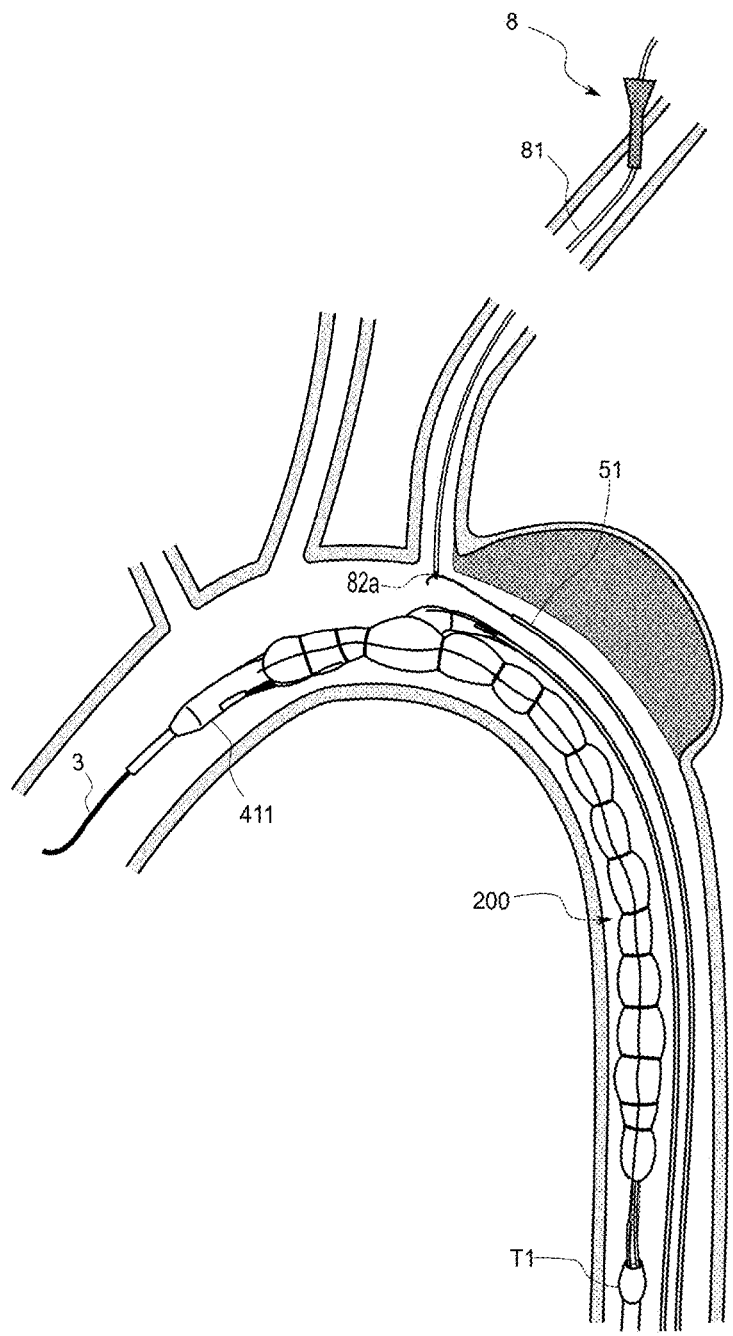

FIG. 27 is a process explanatory view showing a process of indwelling the stent graft in the inside of the blood vessel by making use of the stent graft transport device in accordance with the first embodiment.

Figure 28:
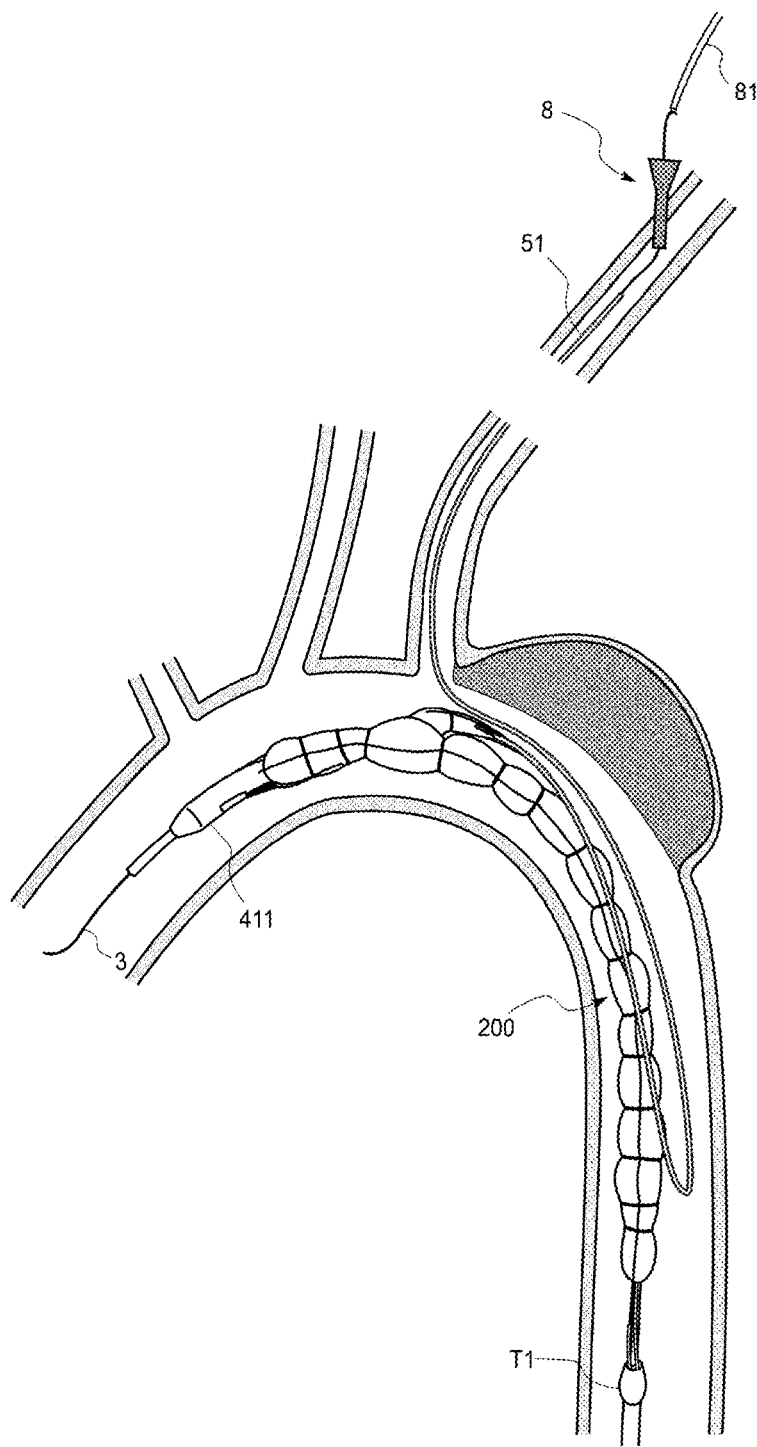

FIG. 28 is a process explanatory view showing a process of indwelling the stent graft in the inside of the blood vessel by making use of the stent graft transport device in accordance with the first embodiment.

Figure 29:
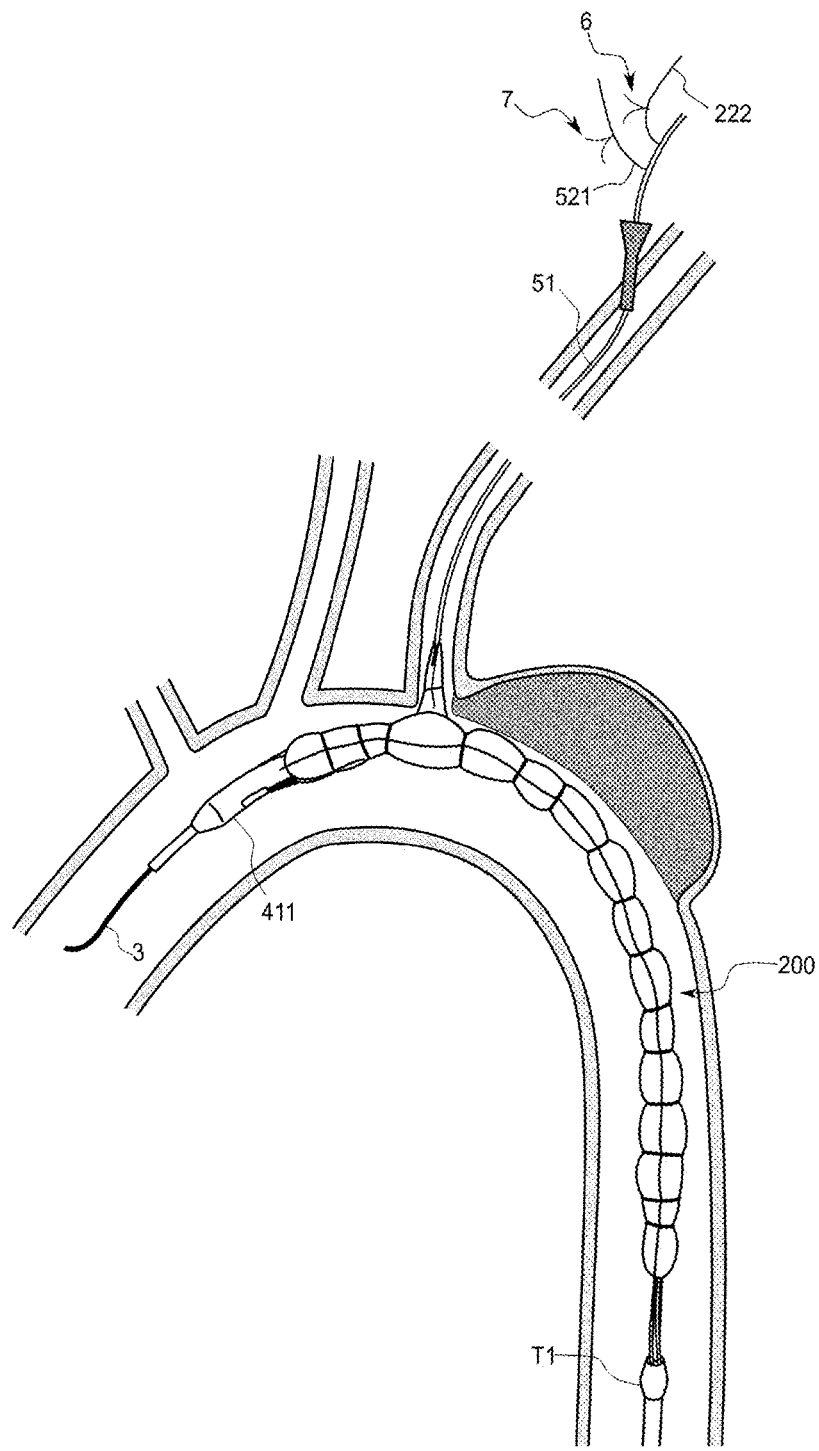

FIG. 29 is a process explanatory view showing a process of indwelling the stent graft in the inside of the blood vessel by making use of the stent graft transport device in accordance with the first embodiment.

Figure 30:
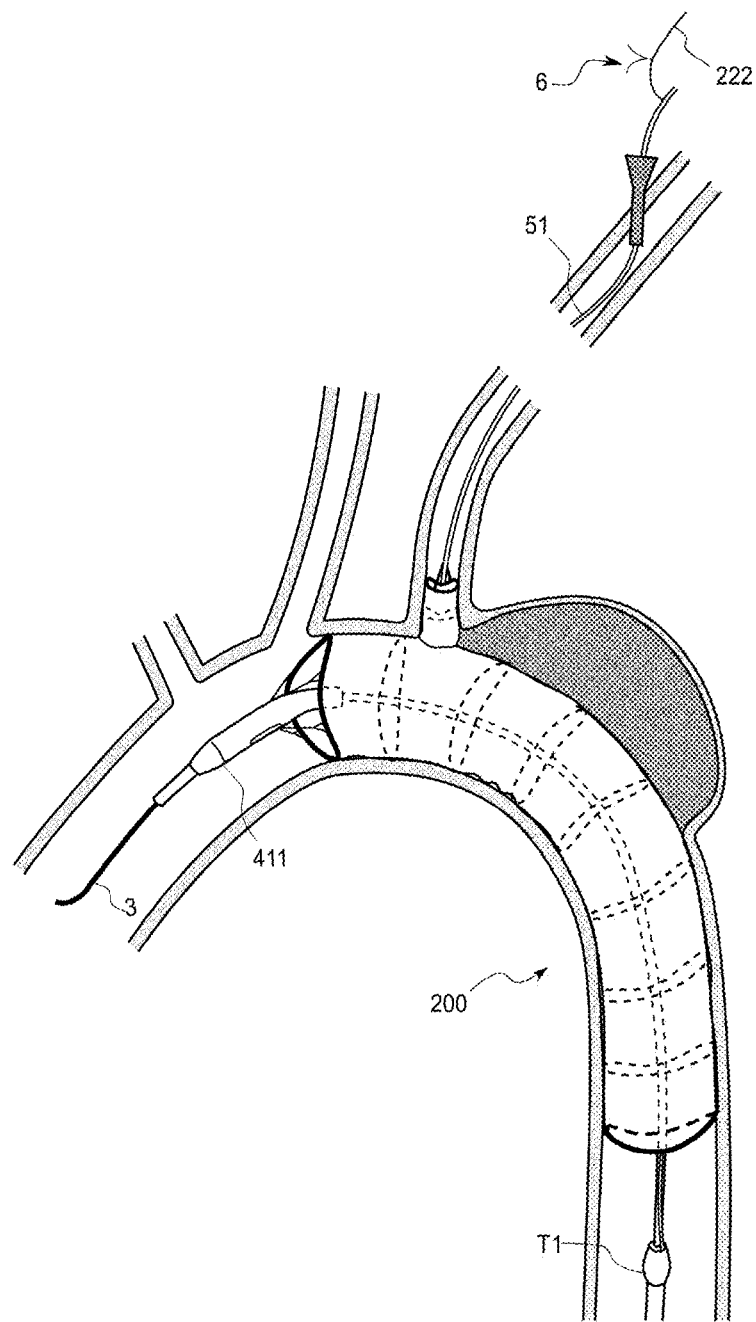

FIG. 30 is a process explanatory view showing a process of indwelling the stent graft in the inside of the blood vessel by making use of the stent graft transport device in accordance with the first embodiment.

Figure 31:
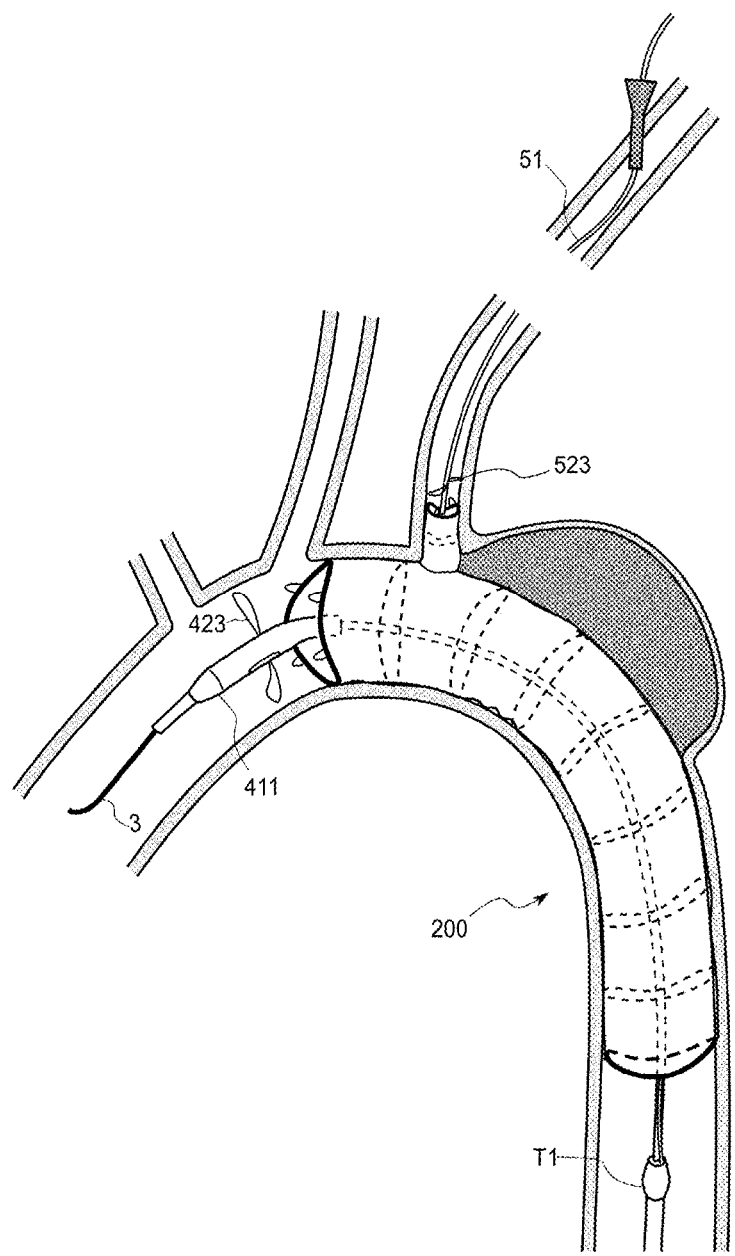

FIG. 31 is a process explanatory view showing a process of indwelling the stent graft in the inside of the blood vessel by making use of the stent graft transport device in accordance with the first embodiment.

Figure 32:
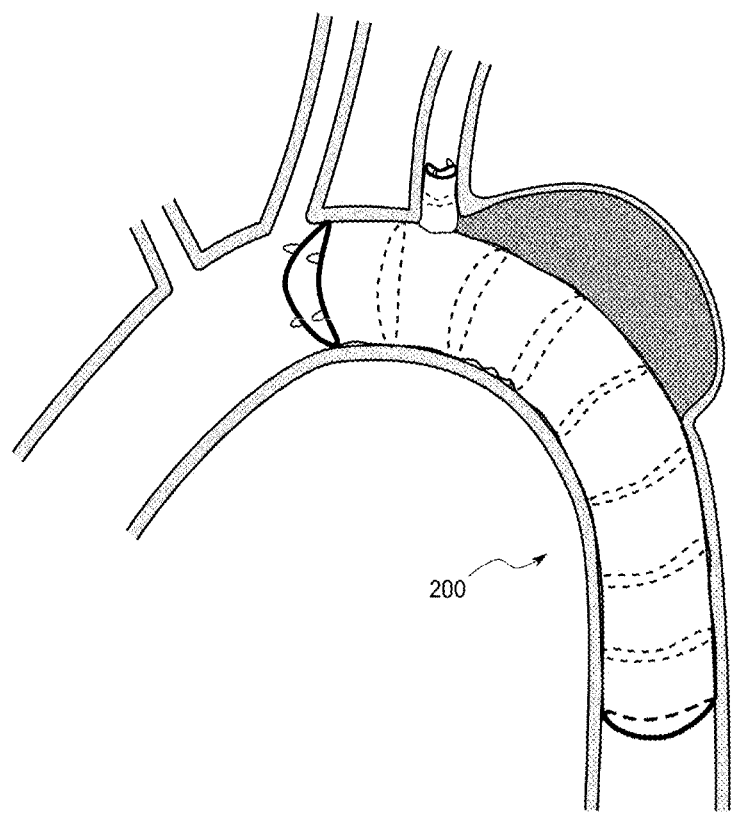

FIG. 32 is a process explanatory view showing a process of indwelling the stent graft in the inside of the blood vessel by making use of the stent graft transport device in accordance with the first embodiment.

Figure 33:
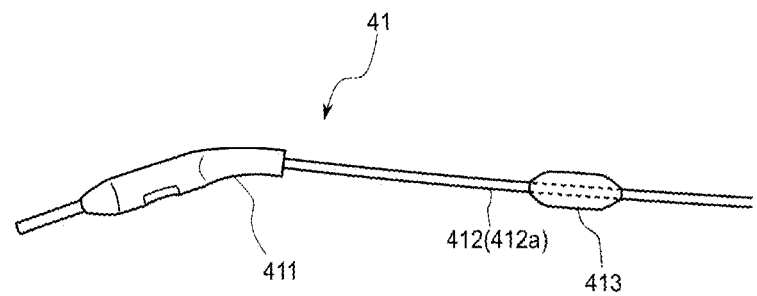

FIG. 33 is a side view showing a second posture control member in accordance with a second embodiment of this invention.

Figure 34:
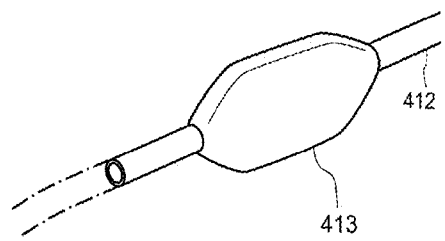

FIG. 34 is a perspective view showing the second posture control member in accordance with the second embodiment.

Figure 35:
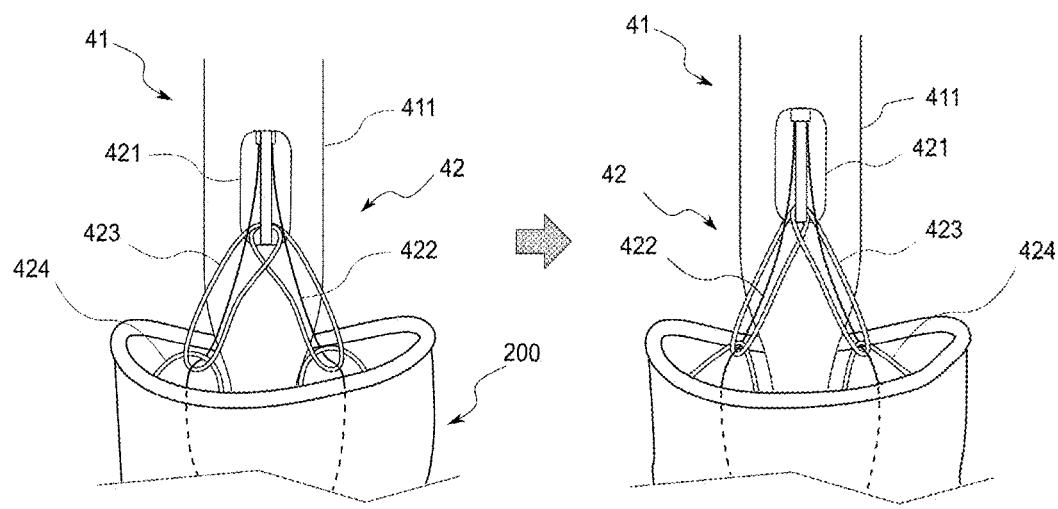

FIG. 35 is a view showing a first mounting mechanism in accordance with a further different embodiment of this invention.

Figure 36:
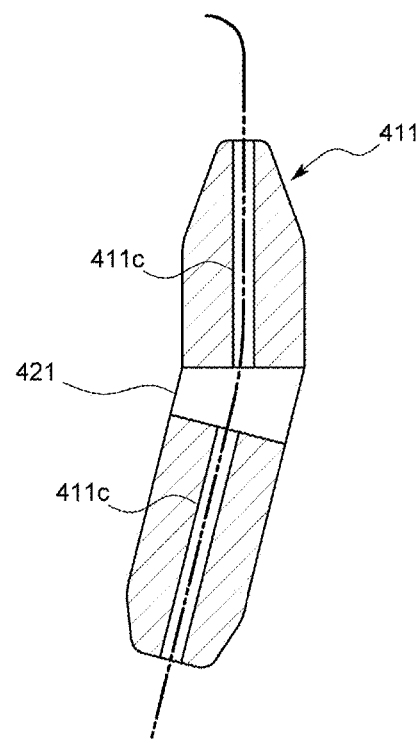

FIG. 36 is a cross-sectional view showing a posture control member in accordance with a further different embodiment of this invention.

Figure 37:
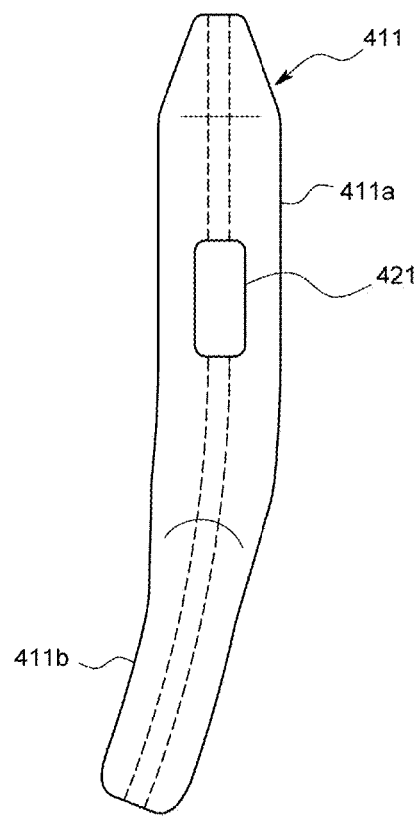

FIG. 37 is a front view showing a posture control member in accordance with a further different embodiment of this invention.

DESCRIPTION OF EMBODIMENTS

One embodiment of this invention will be explained with reference to drawings.

A stent graft transport device 100 in accordance with this embodiment is to transport an artificial blood vessel (a stent graft 200 in this embodiment) to a lesion part through a blood vessel and indwell the artificial blood vessel.

Before explaining the stent graft transport device 100, the stent graft 200 as being an object to be transported will be briefly explained.

<Structure of the Stent Graft 200>

Figure 1:
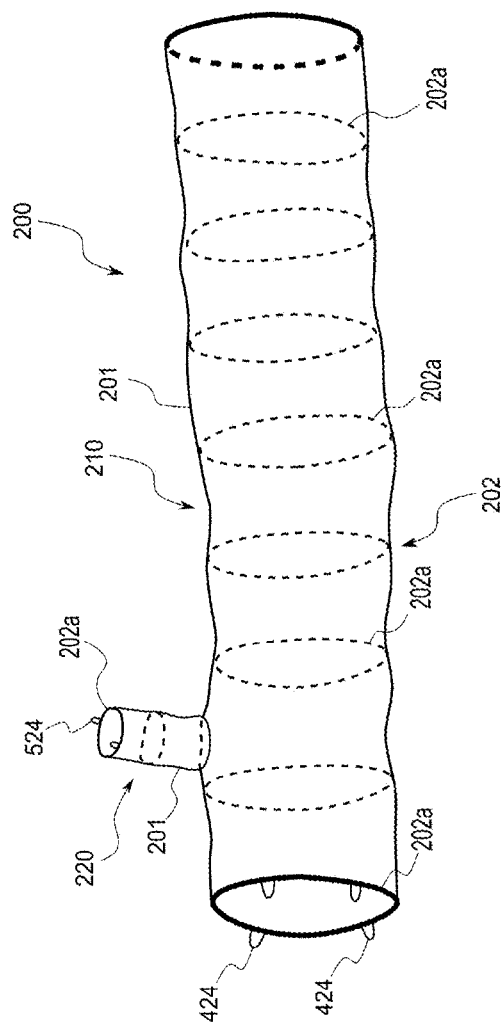
FIG. 1 is a general view of a stent graft in accordance with a first embodiment of this invention.
Figure 2:
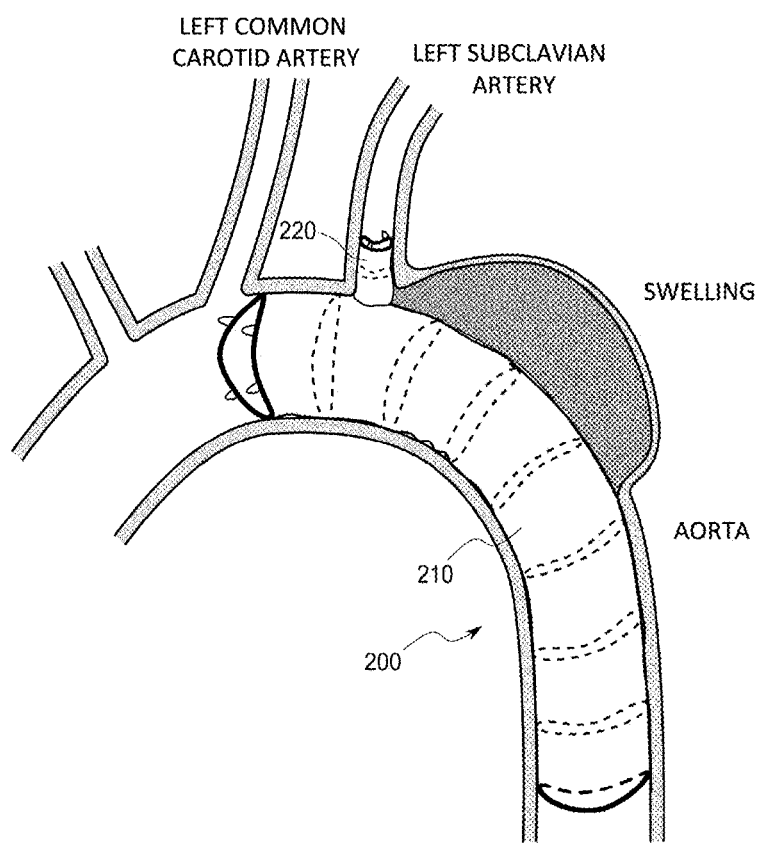
FIG. 2 is a state diagram showing a final indwelled state of the stent graft in accordance with the first embodiment.

The stent graft 200 in accordance with this embodiment is, as shown in FIG. 1 and FIG. 2, a branched shape comprising a long and large diameter main tube 210 and a short and small diameter branch tube 220 that bifurcates from a part of the main tube 210, and is indwelled in, for example, the arch aorta in this embodiment.

The main tube 210 is so arranged that a distal end (an upstream end) thereof is positioned between the left subclavian artery and the left common carotid artery and extends downstream while curving along the arch aorta, and a proximal end (a downstream end) thereof is positioned to locate at a downstream side of the aortic aneurysm. In addition, the branch tube 220 bifurcates and extends from a part of the main tube 210 and is inserted and arranged in the left subclavian artery.

Each of the main tube 210 and the branch tube 220 comprises a tubular graft 201 and a stent 202 to expand the graft 201.

The graft 201 is made of, for example, a durable and having less tissue reaction resin sheet formed to be tubular, and in this embodiment, multiple number of folds (not shown in drawings) are provided beforehand along a circumferential direction of the graft 201 so as to facilitate bending or expansion and contraction along an axis of the graft 201. The material of the sheet may be, for example, a knit fabric of a fiber, a non-woven fabric, or a porous sheet. In addition, a coating treatment of an antithrombotic material such as heparin, collagen, acetylsalicylic acid, or gelatin may be provided on a surface of the sheet constituting the graft 201.

The stent 202 comprises multiple circular elastic rings 202a each of which is arranged from one opening end of the graft 201 to the other opening end thereof at predetermined intervals (at generally uniform intervals in this embodiment, however, they may not be at uniform intervals), and the stent 202 expands into a generally cylindrical shape due to the elastic rings 202a in a natural state. Due to the arrangement wherein each of the circular elastic rings 202a is separately arranged, the stent graft 200 easily bends in the axial direction and has excellent bending performance.

The elastic ring 202a is in a torus shape formed by an ultrafine diameter metal line (not shown in drawings) having predetermined elasticity that is wound at multiple times (multiplex). The material of the elastic ring 202a may be, for example, a metal such as stainless, tantalum, titanium, platinum, gold, tungsten, nickel-titanium, or an alloy of these metals. As mentioned, with the arrangement wherein the elastic ring 202a is made of a thin-diameter metal line that is wound at multiple times, durability is improved compared with an elastic ring made of a single line that is wound at once. In addition, even if the elastic ring 202a gets damaged, it is broken only partially, resulting in obtaining an effect that the function as the elastic ring 202a will not be lost immediately. Similar to the graft 201, the elastic ring 202a may be provided with a coating treatment of an antithrombotic material or may be made of resin.

Other types such as a so called Z stent 202 or a mesh stent may be used in spite of a defect of being less likely to be bent as the stent 202.

Figure 3:
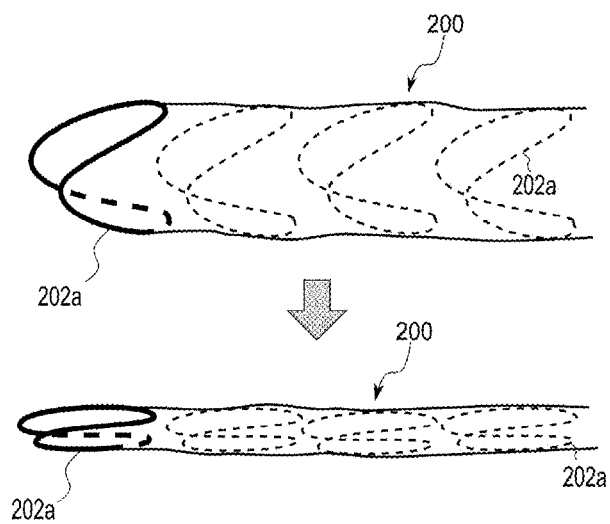
FIG. 3 is a process view showing a process of shrinking the stent graft in accordance with the first embodiment.

Each of the main tube 210 and the branch tube 220 having the above-mentioned arrangement is so configured that each of the elastic rings 202a bends in a saddle shape and accordingly the graft 201 also transforms so as to shrink in the radial direction when an inward external force is applied from an outside in the radial direction. "In a saddle shape" in this embodiment means that the elastic ring 202a bends to a direction to be double-folded, as shown in FIG. 3, and the double-folded elastic ring 202a is further double-folded so that a ridge and a valley appear alternatively two by two.

<Explanation of the Stent Graft Transport Device 100>

Next, the stent graft transport device 100 will be explained.

Figure 4:
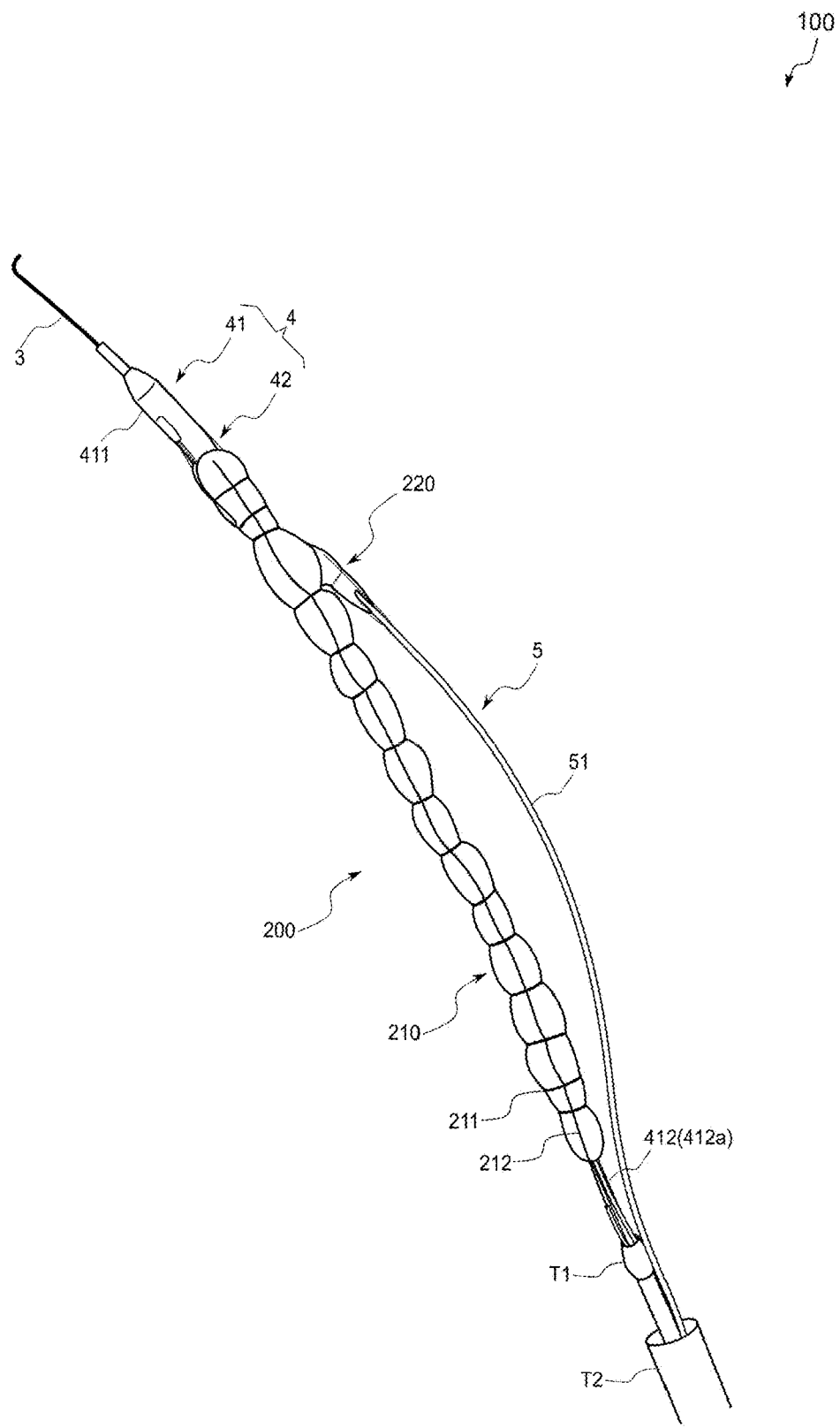
FIG. 4 is a mounting state view showing a state wherein the stent graft in accordance with the first embodiment is mounted on a stent graft transport device.
Figure 5:
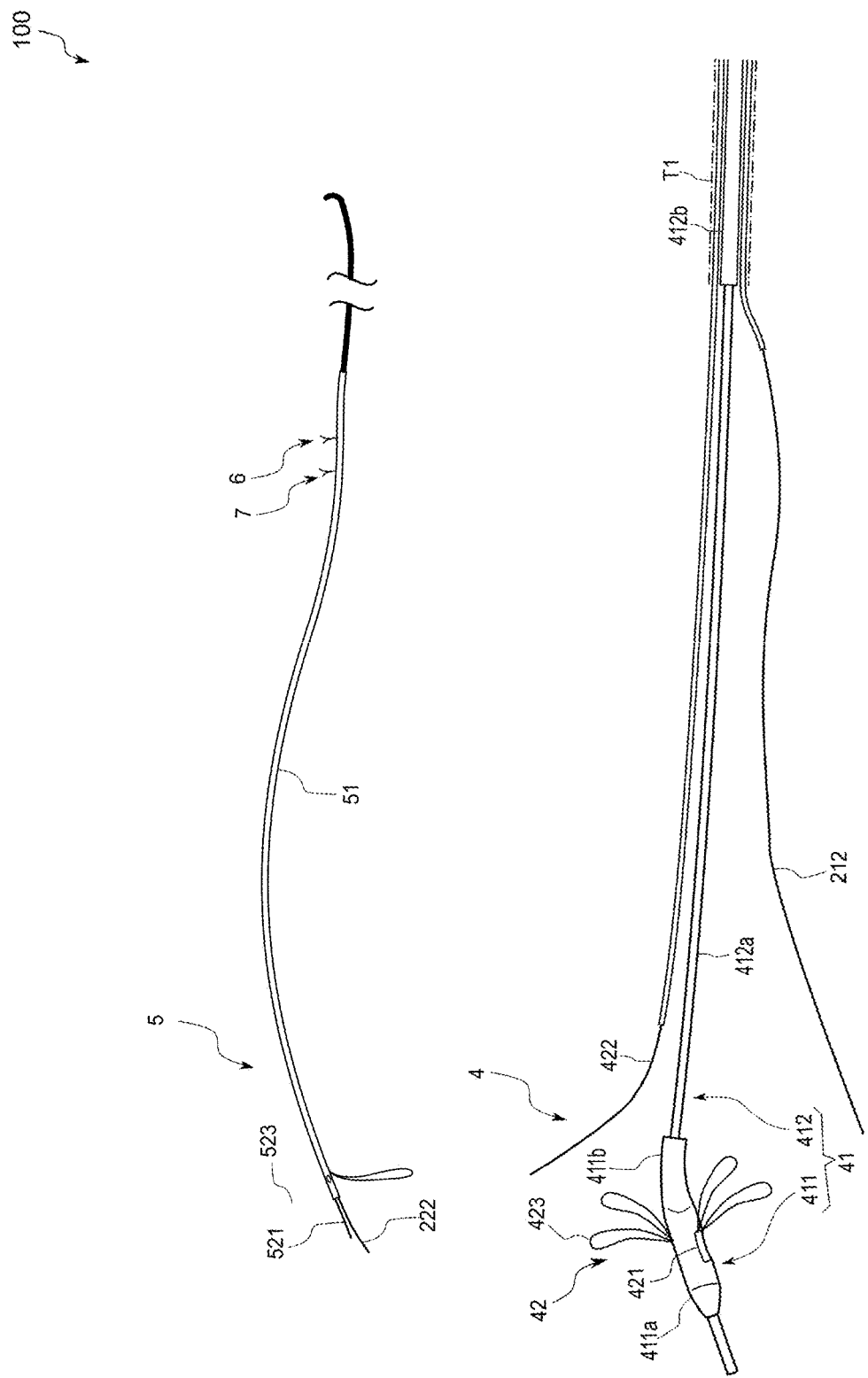
FIG. 5 is an exploded view of the stent graft transport device in accordance with the first embodiment.

The stent graft transport device 100 comprises, as shown in FIG. 4 and FIG. 5, a transport mechanism that transports the stent graft 200 that is shrunk to have a diameter small enough to be inserted into the blood vessel to a predetermined indwelled portion (the arch aorta and the left subclavian artery in this embodiment) and an expansion mechanism that expands the stent graft 200 that is transported to the indwelled portion by the transport mechanism form the shrunk state to the expanded state.

Each part will be explained in detail.

<Transport Mechanism>

The transport mechanism comprises, as shown in FIG. 4 and FIG. 5, a main transport mechanism 4 that transports the contracted stent graft 200 to the arch aorta along the guide wire 3 (a guide wire in claims) inserted into the blood vessel and an auxiliary transport mechanism 5 that inserts the branch tube 220 of the stent graft 200 that is transported to the arch aorta by the main transport mechanism 4 into the left subclavian artery as being the bifurcated blood vessel and arranges the branch tube 220 in the left subclavian artery.

<Main Transport Mechanism 4>

The main transport mechanism 4 comprises, as shown in FIG. 4 and FIG. 5, a tubular body 41 inside of which the guide wire 3 passes in a slidable manner and a first mounting mechanism 42 that mounts the stent graft 200 (the main tube 210 of the stent graft 200) on the tubular body 41 in a removable manner, and is so configured that the tubular body 41 and the stent graft 200 mounted on the tubular body 41 can be transported along the guide wire 3 that passes the aorta.

<Tubular Body 41>

The tubular body 41 comprises, as shown in FIGS. 5, 6A, 6B, and 7, a first transport tube 412 that is in a tube shape inside of which the guide wire 3 passes and a posture control member 411 that is made of resin and mounted on a distal end part of the first transport tube 412. The stent graft 200 is externally mounted on the tubular body 41 and a distal end part of the stent graft 200 grasps the posture control member 411 so that the stent graft 200 is mounted on the tubular body 41.

The posture control member 411 is long and thin, and comprises a cylindrical header 411a whose distal end part is tapered to be generally conical and a flat mounting body 411b that integrally elongates from a rear end of the header 411a. A length of a longitude direction of the posture control member 411 is shorter than or equal to one fourth of the length of the longitude direction of the stent graft 200 (the main tube 210), and shorter than that of the main tube 210.

The reason why the distal end part of the header 411a is made to be conical is to make it possible for the posture control member 411 to smoothly proceed in the blood vessel. On the other hand, a proximal end (a peripheral part on the proximal end surface, in this embodiment) of the mounting body 411b is smoothly rounded not to be angular. This is to make it difficult for the posture control member 411 to be caught by the blood vessel when the posture control member 411 is pulled after the stent graft 200 is indwelled.

On the other hand, the reason why the mounting body 411b is made to be flat is to make it sure to co-rotate the main tube 210 and the posture control member 411 in a state wherein a distal end opening of the contracted main tube 210 grasps the mounting body 411b.

Figure 6A:
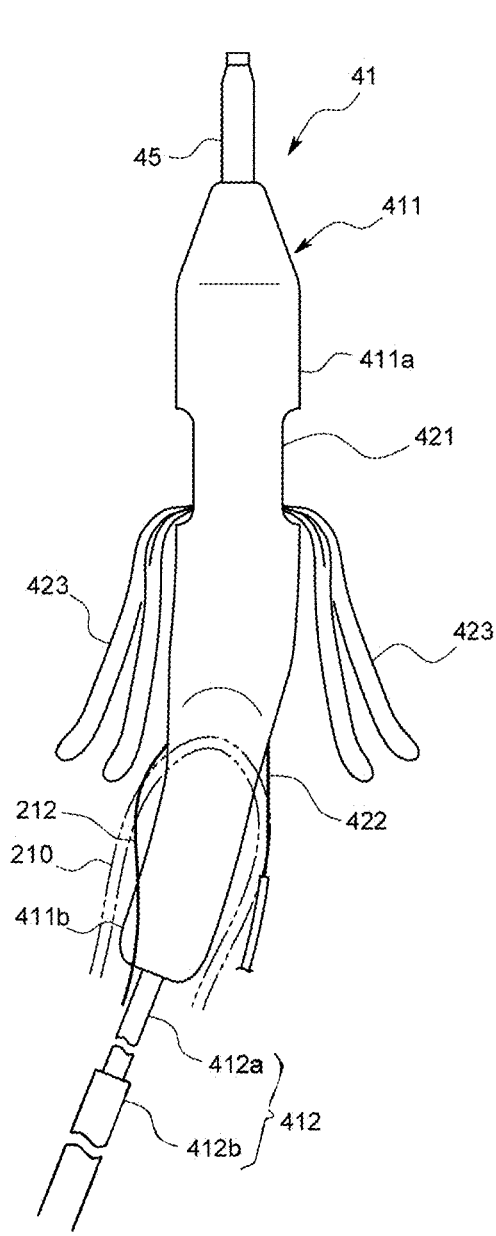
FIGS. 6A and 6B are a front view and a side view, respectively, showing a tubular body (a posture control member) in accordance with the first embodiment.
Figure 6B:
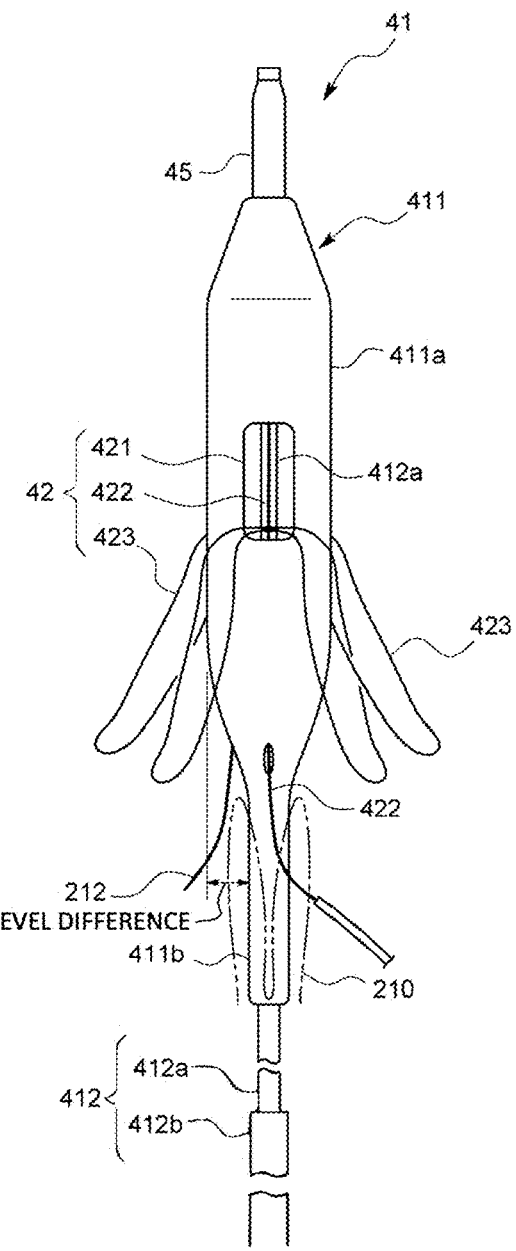

In addition, since a level difference is generated between the flat mounting body 411b and the cylindrical header 411a so that a height of the level difference is set to be more than or equal to a diameter of the elastic ring 202a of the main tube 210, as shown in FIG. 6B, the distal end part of the main tube 210 that grasps the mounting body 411b hides in the level difference viewed from the front. With this arrangement, since it is possible to inhibit the opening distal end part of the main tube 210 from getting stuck in the blood vessel during transporting the stent graft 200, smooth transportation can be secured.

Figure 7:
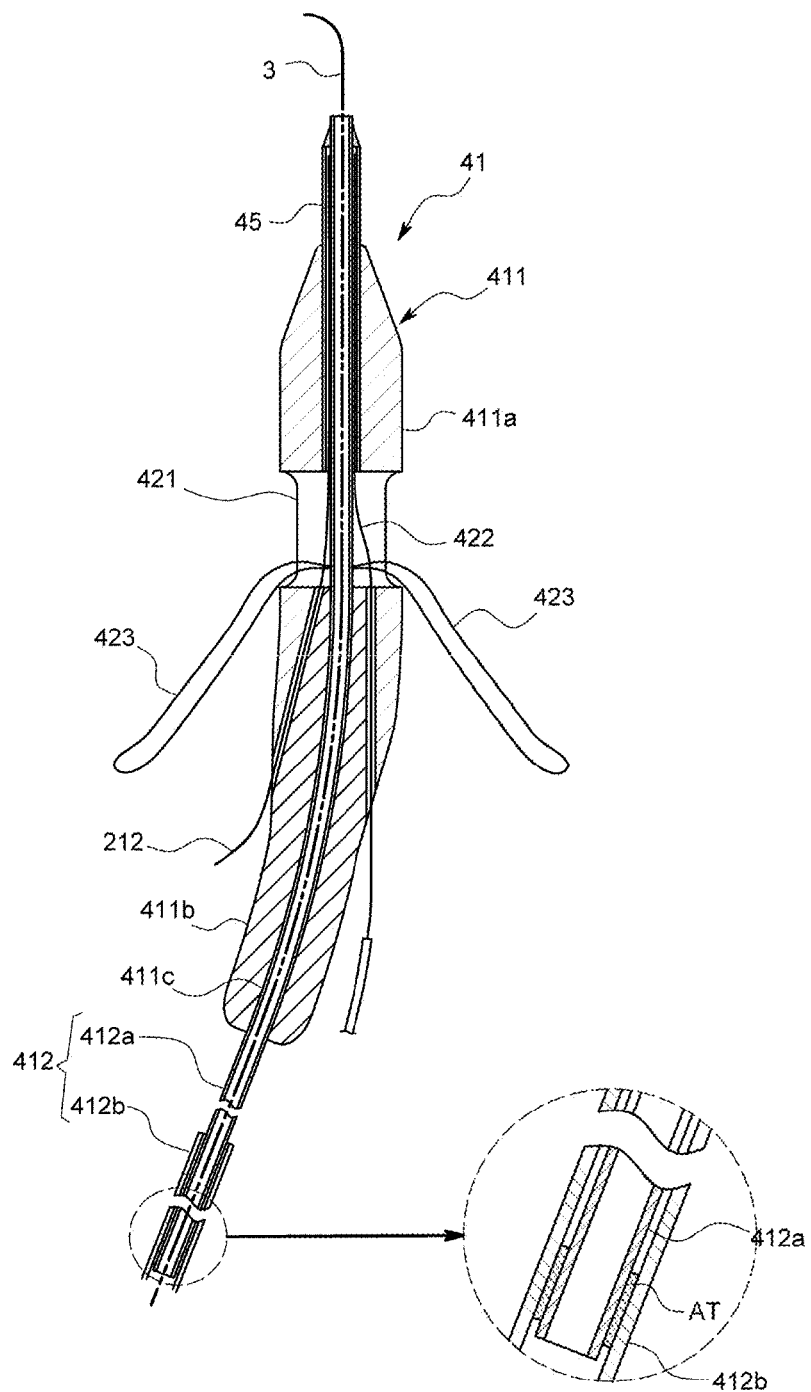
FIG. 7 is a longitudinal sectional view of the tubular body (the posture control member) in accordance with the first embodiment.

Furthermore, as shown in FIG. 7, a through bore 411c where the guide wire 3 is inserted is provided in a longitudinal direction of the posture control member 411. In this embodiment, a part of the through bore 411c where the mounting body 411b is inserted is mainly curved and a part where the header 411a passes is generally straight. Then, in this embodiment, the mounting body 411b is a little curved to be a fan shape.

Conversely, a part of the through bore 411c where the header 411a passes may be slightly curved, or the entire through bore 411c may be curved.

The first transport tube 412 comprises, as shown in FIGS. 6A, 6B, and 7, an inner tube 412a and an outer tube 412b, and is a double pipe structure wherein the inner tube 412a projects from a distal end part of the outer tube 412b.

The inner tube 412a is a two-layer structure made of, for example, polyimide and PTFE, and is more elastic and easily twisted than the outer tube 412b. Then, the posture control member 411 is connected to a distal end part of the inner tube 412a. Specifically, the distal end part of the inner tube 412a is adhered to the posture control member 411 in a state wherein the distal end part of the inner tube 412a passes the through bore 411c. A length of a part of the inner tube 412a projecting from the outer tube 412b is set to be longer than a total length of the posture control member 411 and the stent graft 200 mounted on the posture control member 411. As a result, the distal end of the outer tuber 412b is separately arranged from the rear end of the stent graft 200 rearward (operator side) so that the inner tube 412a is exposed between the distal end of the outer tube 412b and the rear end of the stent graft 200.

The outer tube 412b is made of, for example, polyimide, and a rigidity of the outer tube 412b is higher than that of the inner tube 412a.

Figure 9:
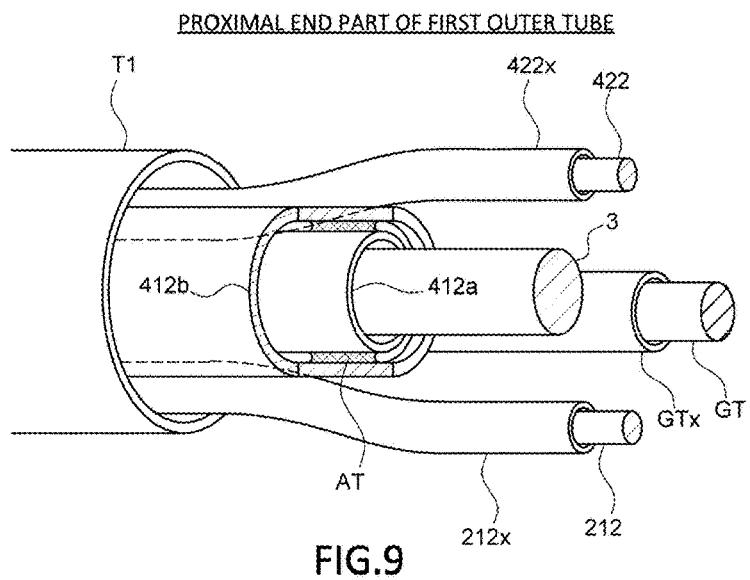
FIG. 9 is a perspective view showing the tubular body, the first engaging wire and the first control wire, all of which extend from an operator's side of the first outer tube in accordance with the first embodiment.
Figure 10:
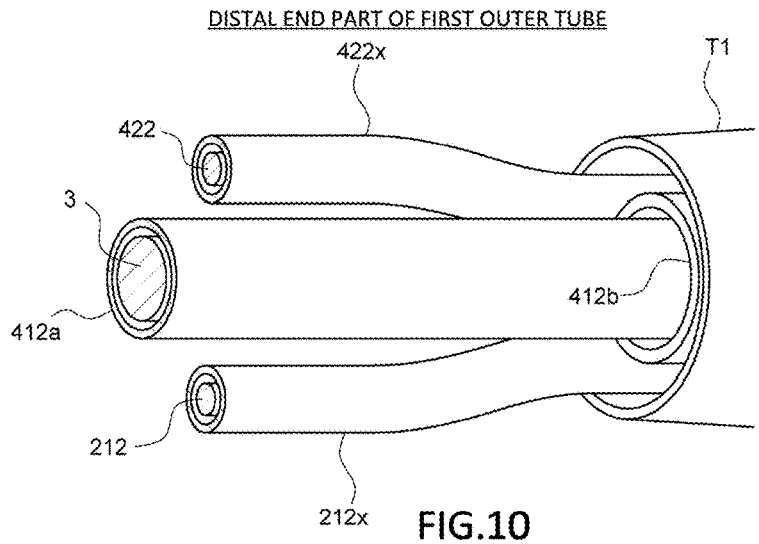
FIG. 10 is a perspective view showing the tubular body, the first engaging wire and the first control wire, all of which extend from a distal end side of the first outer tube in accordance with the first embodiment.

As shown in FIG. 7 and FIG. 9, the outer tube 412b and the inner tube 412a are adhered to each other by an adhesive agent (AT) only on the operator's side farther from the distal end of the outer tube 412b, specifically, only in the vicinity of a part operated by the operator.

<First Mounting Mechanism 42>

The first mounting mechanism 42 is a mechanism to detachably mount the main tube 210 of the stent graft 200 on the tubular body 41, more specifically on the posture control member 411.

A specific explanation is as follows.

The first mounting mechanism 42 makes use of, as shown in FIGS. 6A, 6B, 7, and 11, a first window 421 arranged on an outer peripheral surface of the posture control member 411, a first engaging wire 422 inserted into the inside of the first window 421, a plurality of first detachable strings 423 whose proximal end part is mounted on the tubular body 41 (the posture control member 411 in this embodiment), and a plurality of first string insertion holes 424 arranged on a distal end opening edge part of the main tube 210.

The first window 421 is formed by cutting a part of a side peripheral surface of the header 411a. A penetrating direction of the first window 421 coincides with, as shown in FIGS. 6A 6B, 7, and 11, a bending direction of the posture control member 411, in this embodiment, however, the penetrating direction may be orthogonal to the bending direction as shown in FIG. 37. If the penetrating direction is orthogonal to the bending direction as shown in FIG. 37, the opening end of the first window 421 is difficult to be directly contacted with a greater curvature side of the blood vessel, thereby reducing a possibility of hurting the blood vessel.

The first engaging wire 422 is a thin line made of metal or resin.

The first detachable string 423 is so configured that at least a ring is formed on a distal end part thereof (all are formed to be rings in this embodiment), and a proximal end part thereof is mounted on the tubular body 41.

Specifically explained, the proximal end part of the first detachable string 423 is wound around the first transport tube 412 (the inner tube 412*a*) so as to be mounted on the first transport tube 412 that penetrates the first window 421, and the distal end part thereof is drawn out to the outside through the first window 421. As another embodiment, the proximal end part of the first detachable string 423 may be fixed to the posture control member 411 by an adhesive agent or the like. In this embodiment, four first detachable strings 423 having this arrangement are provided.

The above-mentioned first string insertion hole 424 is formed by mounting a ring-shaped string on the distal end opening edge part of the main tube 210, and four first string insertion holes 424 are formed at even intervals in this embodiment.

Next, how the tubular body 41 is mounted on the main tube 210 by the use of the first mounting mechanism 42 will be explained.

Figure 11:
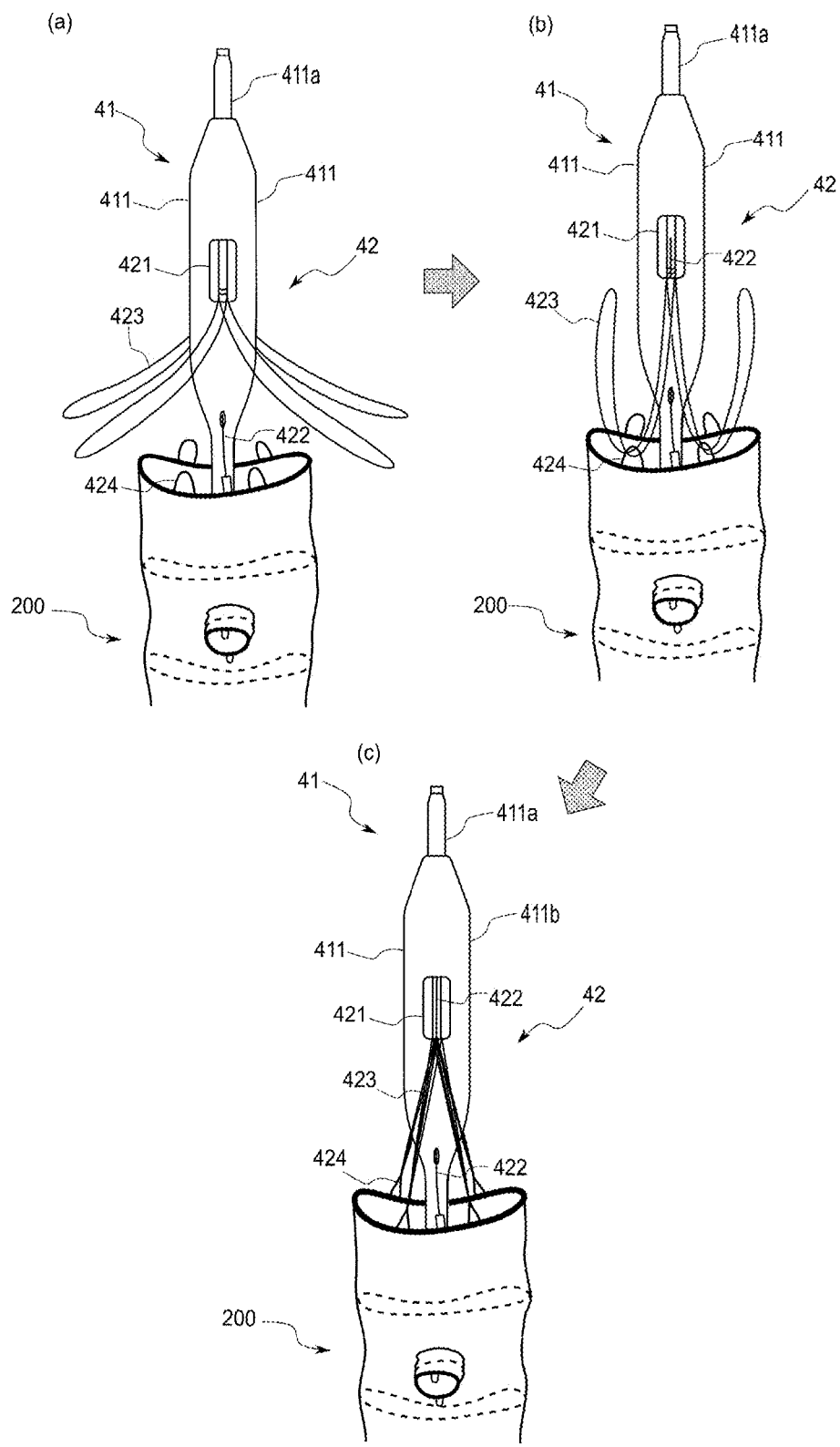
FIG. 11 is a process explanatory view showing a process of mounting the stent graft on the tubular body by a first mounting mechanism in accordance with the first embodiment.
Figure 12:
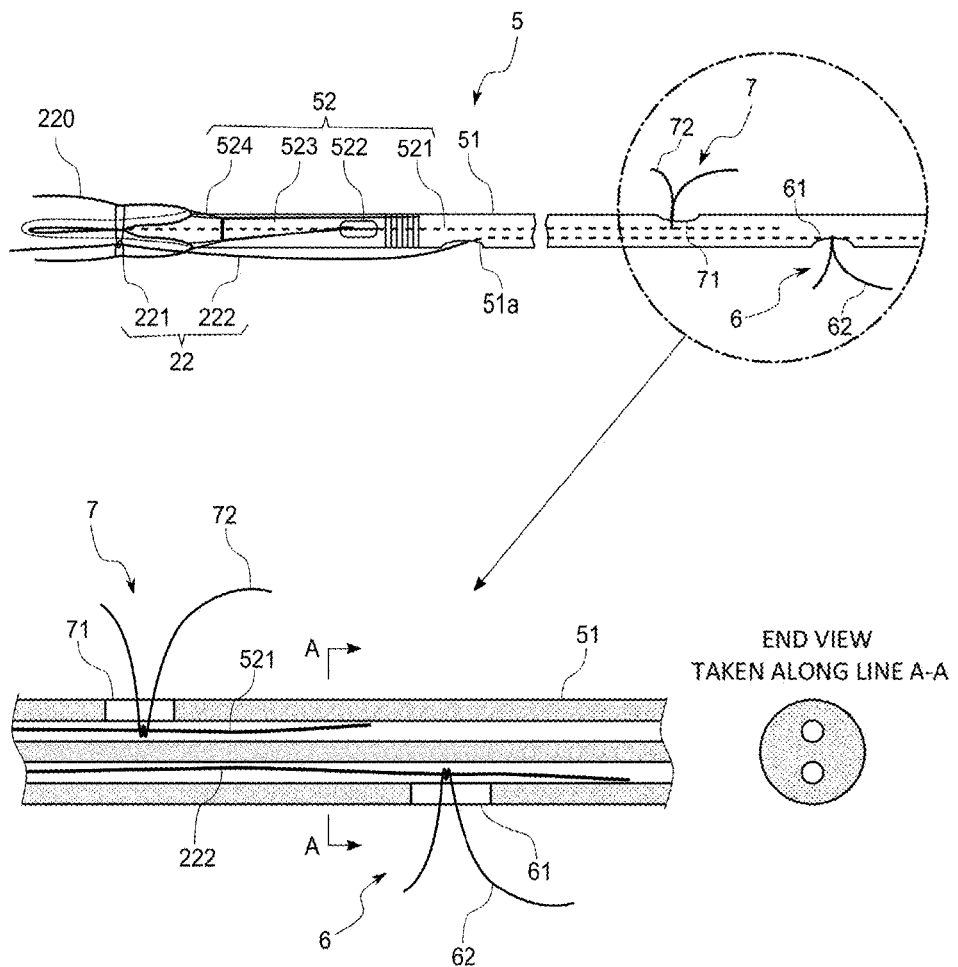
FIG. 12 is a partial side view showing a second mounting mechanism, a second expansion mechanism, a control wire pulling-out mechanism, and an engaging wire pulling-out mechanism in accordance with the first embodiment.

As shown in steps (a) to (c) of the process of FIG. 11, a distal end of each of the four first detachable strings 423 passes the first string insertion hole 424 arranged at each of the four portions of the opening edge part of the main tube 210, respectively, and the ring formed on the distal end of the detachable string 423 that passes the first string insertion hole 424 passes the first window 421 and then is hooked by the first engaging wire 422 arranged inside of the first window 421. Then the main tube 210 is mounted on the posture control member 411 through the first detachable string 423.

In case of dismounting the main tube 210 from the posture control member 411 (the tubular body 41), an operator should pull the proximal end part of the first engaging wire 422. In accordance with this operation, the distal end of the first engaging wire 422 moves to the operator's side from the first window 421 and then the ring formed on the distal end of the first detachable string 423 is dismounted from the first engaging wire 422 and returns to the state shown at step (a) in FIG. 11 so that the main tube 210 is in a state of being able to be dismounted from the posture control member 411 (the tubular body 41).

A number of the first detachable strings may not be the same as that of the first string insertion holes. For example, in a case in which four first string insertion holes are provided such as the present embodiment, the number of the first detachable strings may be less than that of the first string insertion holes, namely only one, and the first detachable string may pass all of the first string insertion holes and then the ring formed on the distal end of the first detachable string may be hooked on the first engaging wire. In addition, two first detachable strings may be provided and each of the detachable strings may pass two mutually different first string insertion holes, respectively.

<The Auxiliary Transport Mechanism 5>

The auxiliary transport mechanism 5 is, as shown in FIG. 4, FIG. 5, and FIGS. 12 to 16, configured to insert and indwell the branch tube 220 in the bifurcated blood vessel (the left subclavian artery in this embodiment), and comprises a second transport tube 51 (corresponds to the transport tube in claims) and a second mounting mechanism 52 to detachably mount the branch tube 220 on the second transport tube 51.

<Second Transport Tube 51>

The second transport tube 51 is a flexible tube having a small diameter with a plurality of lumens (two lumens are illustrated in the present embodiment; however, there may be three or more lumens), and a proximal end part of the second transport tube 51 is mounted on an opening part of the branch tube 220.

<Second Mounting Mechanism 52>

The second mounting mechanism 52 makes use of a second engaging wire 521 (a mounted state keeping wire in claims) that passes inside of the second transport tube 51, a second window 522 arranged on an outer peripheral surface of the second transport tube 51, one or a plurality of second detachable strings 523 (one in this embodiment) mounted on the second transport tube 51 and a plurality of second string insertion holes 524 (two in this embodiment) arranged at a distal end opening edge part of the branch tube 220, and has the same principle as that of the first mounting mechanism 42.

More specific explanation will follow.

The second engaging wire 521 is made of a metal or a resin that can be pushed or drawn by the operator, and is inserted into one of the lumens (hereinafter called as the first lumen) of the second transport tube 51.

The second window 522 is formed by cutting part of a side surface of the second transport tube 51 so as to be in communication with the first lumen, and the second engaging wire 521 that passes the first lumen is exposed from the second window 522.

The second detachable string 523 is so configured that a ring (all are formed to be rings in this embodiment) is formed at least at a distal end part thereof, and a proximal end part thereof is fixed to near the second window 522 (a downstream side of the second window 522 in this embodiment) of the second transport tube 51 by an adhesive agent or the like.

The second string insertion hole 524 is formed by mounting a string formed to be circular at the distal end opening edge part of the branch tube 220.

In accordance with the second mounting mechanism 52 having the above arrangement, the branch tube 220 is mounted on the second transport tube 51 in the following manner.

More specifically, a distal end of each of the second detachable strings 523 is inserted into and continuously passes through the second string insertion holes 524 arranged at two portions of the opening edge part of the branch tube 220. Then, the ring formed on the distal end of the second detachable strings 523 that is inserted into and passes through each of the second string insertion holes 524 is inserted into and passes through the second window 522 and then is hooked by the second engaging wire 521 arranged inside of the second window 522. As mentioned, the branch tube 220 is mounted on the second transport tube 51 through the second detachable strings 523.

In case of dismounting the branch tube 220 from the second transport tube 51, the second engaging wire 521 is pulled. With this operation, the ring formed on the distal end of the second detachable string 523 is dismounted from the second engaging wire 521 so that the branch tube 220 becomes in a state of being able to be separated from the second transport tube 51.

<Expansion Mechanism>

An expansion mechanism is to expand the stent graft 200 that is transported to the indwelled position in a contracted state in a radial direction and to tightly adhere the stent graft 200 to the inside of the blood vessel. The expansion mechanism in this embodiment comprises a first expansion mechanism 21 for the main tube 210 and a second expansion mechanism 22 for the branch tube 220.

<First Expansion Mechanism 21>

The first expansion mechanism 21 comprises, as shown in FIG. 4 and FIG. 17, a first binding string 211 that keeps a contracted state of the main tube 210 by binding the outer circumferential surface of the main tube 210 and a first control wire 212 that is made of metal or resin and that controls a binding and releasing state of the first binding string 211.

The first binding string 211 is, for example, an endless annular shape and the first binding string 211 is folded in half to be a double line and wraps around the contracted main tube 210 such that both end parts of the two-folded first binding string 211 overlap each other at a time of binding the main tube 210. Then the first control wire 212, being the thin wire extending in the axial direction made of metal or resin, is inserted into a ring formed by the overlapped two-folded first binding string 211. In accordance with this arrangement, as shown in step (a) of the process of FIG. 17, both end parts of the first binding string 211 are prevented from being separated so that the main tube 210 is kept in a bound state.

Then, when the first control wire 212 is drawn out in the bound state, the bound state of the both end parts of the first binding string 2 is released, as shown in step (b) of FIG. 17, so that the bound state of the main tube 210 is released.

In this embodiment, as shown in FIG. 4, a plurality of first binding strings 211 are intermittently provided along the axial direction of the main tube 210, and the first control wire 212 is inserted into each of the first binding strings 211 that bind the main tube 210.

Then, if the first control wire 212 is pulled out, all of the first binding strings 211 that bind the main tube 210 are released so that the main tube 210 becomes in an expanded state due to an elastic restoring force of the stent 202 (each elastic ring 202a).

<Second Expansion Mechanism 22>

The second expansion mechanism 22 comprises, as shown in FIGS. 12 to 16, a second binding string 221 that keeps a contracted state of the branch tube 220 by binding an outer circumferential surface of the branch tube 220 and a second control wire 222 (a contracted state keeping wire in claims) that is made of metal or resin and that controls a binding and releasing state of the second binding string 221.

The second binding string 221 has the same configuration as that of the first binding string 211, so an explanation will be omitted.

The second control wire 222 is inserted into and passes another lumen (hereinafter called as a second lumen) of the second transport tube 51. A distal end part of the second control wire 222 is exposed to the outside of the side surface bore 51a arranged in a middle of the second transport tube 51 and is inserted into and passes a loop part of the second binding string 221 that binds the branch tube 220.

In this embodiment, both the second engaging wire 521 and the second control wire 222 are inserted into the second transport tube 51, and the whole second engaging wire 521 is housed inside of the second transport tube 51 and the whole second control wire 222 is also housed inside of the second transport tube 51 except for the distal end part thereof to keep the bound state of the branch tube 220.

The reason why at least each proximal end part of the second engaging wire 521 and the second control wire 222 is housed inside of the second transport tube 51 will be described later in <usage>. The reason is because the second transport tube 51 including an operator's end part (a proximal end part) is drawn around inside of the blood vessel during an operation. The arrangement is to securely prevent the second control wire 222 and the second engaging wire 521 from being unexpectedly pulled and prevent the expansion mechanism or the mounting mechanism from being unexpectedly operated.

<Pulling-Out Mechanism>

On the other hand, if the second control wire 222 and the second engaging wire 521 cannot be pulled out from the second transport tube 51, since it is not possible to operate the second expansion mechanism 22 and the second mounting mechanism 52, a pulling-out mechanism to pull out the second control wire 222 and a pulling-out mechanism to pull out the second engaging wire 521 are provided respectively in this embodiment.

As shown in FIGS. 12 to 16, as the pulling-out mechanism, there are a control wire pulling-out mechanism 6 (a contracted state keeping wire pulling-out window in claims) to pull out the second control wire 222 and an engaging wire pulling-out mechanism 7 (a mounted state keeping wire pulling-out mechanism in claims) to pull out the second engaging wire 521, and both have the same principle.

The control wire pulling-out mechanism 6 comprises a control wire pulling-out window 61 (a contracted state keeping wire pulling-out window in claims) that is arranged in the middle (more specifically, the operator's hand end part) of the second transport tube 51 and a very flexible control wire pulling-out string 62 (a contracted state keeping wire pulling-out string in claims) that is tied to the second control wire 222 and that is pulled out of the second transport tube 51 from the control wire pulling-out window 61.

If the control wire pulling-out string 62 is pulled, the operator's hand side of the second control wire 222 in the second transport tube 51 is pulled out from the control wire pulling-out window 61, and it is possible to expand the branch tube 220 by pulling the pulling-out second control wire 222.

The same applies also to the engaging wire pulling-out mechanism 7. More specifically, the engaging wire pulling-out mechanism 7 comprises an engaging wire pulling-out window 71 (a mounted state keeping wire pulling-out window in claims) that is arranged in the middle (more specifically, the operator's hand end part) of the second transport tube 51 and that is arranged at a portion (a portion deviated in the axial direction in this embodiment) different from the portion where the control wire pulling-out window 61 is arranged and an engaging wire pulling-out string 72 (a mounted state keeping wire pulling-out string in claims) that is tied to the second engaging wire 521 and that is pulled out of the second transport tube 51 from the engaging wire pulling-out window 61.

Although a distal end part of the control wire pulling-out string 62 and a distal end part of the engaging wire pulling-out string 72 are exposed out from the second transport tube 51, since the control wire pulling-out string 62 and the engaging wire pulling-out string 72 are more flexible than the second control wire 222 and the second engaging wire 521 and are not loop-shaped having an open end shape, there is little possibility that the control wire pulling-out string 62 and the engaging wire pulling-out string 72 will unexpectedly get stuck in any portion during the operation.

<Usage>

Next, an example of transporting and indwelling the stent graft 200 by this transport device will be explained.

First, the main tube 210 is contracted and the distal end opening of the contracted main tube 210 holds the posture control member 411 in a state wherein the tubular body 41 is inserted into the main tube 210 of the stent graft 200, and the main tube 210 is mounted on the posture control member 411 by the first mounting mechanism 42.

Similar to the branch tube 220 of the stent graft 200, the branch tube 220 is contracted in a state wherein the second transport tube 51 is inserted into the branch tube 220 of the stent graft 200 and the branch tube 220 is mounted on the second transport tube 51 by the second mounting mechanism 52.

Furthermore, the guide wire 3 is inserted into the tubular body 41 (the first transport tube 412 and the posture control member 411), and the tubular body 41 and the stent graft 200 that is mounted on the tubular body 41 are made to be in a state of being able to be transported along the guide wire 3.

In this state, as shown in FIG. 4, the posture control member 411 is mounted on the distal end part of the main tube 210 of the stent graft 200 and the first transport tube 412, the first engaging wire 422 and the first control wire 212 extend from the main tube 210 and the second transport tube 51 extends from the distal end of the branch tube 220. In addition, the distal end part of the first engaging wire 422 and the distal end part of the first control wire 211 are, as shown in FIGS. 6A, 6B, and 7, inserted into and pass the inside of the posture control member 411, and are housed in a triple lumen tube 45 arranged at a distal end part of the posture control member 411. The arrangement is to prevent a defect that these distal end parts get stuck unexpectedly inside of the blood vessel.

Figure 8:
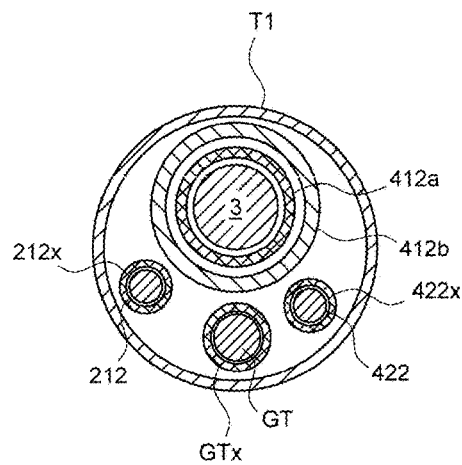
FIG. 8 is a cross sectional view showing a first transport tube, a first engaging wire and a first control wire, all of which are placed in a first outer tube in accordance with the first embodiment.

In this embodiment, the tubular body 41, the first engaging wire 422, and the first control wire 212 that extend from the stent graft 200 are gathered into one piece and inserted into and pass a first outer tube T1 whose diameter is larger than a diameter of the total diameter of the tubular body 41, the first engaging wire 422, and the first control wire 212. In addition, as shown in FIG. 8 and FIG. 9, the first outer tube T1 is so made that a reinforcing wire (GT) made of metal or resin whose rigidity is higher than that of other wire can be detachably inserted into the first outer tube T1, and the first outer tube T1 and the tubular body 41 that are inserted into and pass the inside of the first outer tube T1 are prevented from being buckled or contracted during sending the stent graft 200 forward. Furthermore, in this embodiment, the tube 422x into which the first engaging wire 422 is inserted, the tube 212x into which the first control wire 212 is inserted, the tube (GTx) into which the reinforcing wire (GT) is inserted and the outer tube 412b are adhered to the first outer tube T1 by pouring an adhesive agent (not shown in drawings) at a distal end part and a proximal end part (a root part) of the first outer tube T1.

Then, the stent graft 200, the tubular body 41, the first engaging wire 422, and the first control wire 212, each of which extends from the stent graft 200, (the first outer tube T1 to bind the tubular body 41, the first engaging wire 422, and the first control wire 212) and the second transport tube 51 are inserted into a sheath catheter T2, and as shown in FIG. 18, and only the header 411a projects from a distal end of the sheath catheter T2 in an initial state. A check valve to prevent a blood reverse flow is provided at a root portion of some tubes such as the first outer tube T1 as necessary.

Next, as shown in FIG. 19, the sheath catheter T2 that houses the stent graft 200 and the stent graft transport device 100 is inserted into the inside of the anterior descending artery along the guide wire 3 that precedingly passes in the inside of the artery.

Later, as shown in FIGS. 20 to 22, the stent graft 200 mounted on the posture control member 411 is made to project and be separated from the sheath catheter T2 and then be guided by the guide wire 3 so as to be moved to the indwelled position by sending the first outer tube T1 and the second transport tube 51.

During this process, at a time when the guide wire 3 passes the curved arch aorta, the posture control member 411 naturally rotates in the axial direction (as shown in FIGS. 20 and 21) so as to coincide the curved direction of the posture control member 411 with the curved direction of the arch aorta, and then a phase around the axis of the posture control member 411 is automatically adjusted to be always constant to the blood vessel.

Then, the stent graft 200 fixed to the posture control member 411 also rotates together with the posture control member 411 and is automatically adjusted to a predetermined rotational phase, namely a final indwelled phase.

Then, in the final indwelled phase shown in FIG. 22, since the stent graft 200 is mounted on the posture control member 411 beforehand so as to coincides a position of the branch tube 220 of the stent graft 200 with a position of the branch artery viewed from the axial direction, it is possible to automatically coincide the phase of the branch tube 220 with the phase facing to an entrance of the branch artery without operating the branch tube 220 of the stent graft 200 by the operator. This is a self-alignment function.

Accordingly, it is enough for the operator just to operate the stent graft 200 back and forth so as to locate the branch tube 200 near the entrance of the branch artery, and then it is possible for the operator to coincide the position of the branch tube 220 with the position of the branch artery without operating the stent graft 200 at the operator's side so that the operability can be drastically improved compared with a conventional stent graft.

In addition, since the posture control member 411 is short and mounted only at the distal end part of the stent graft 200 so that the posture control member 411 will not hamper flexibility of the stent graft 200 as being a characteristic of this kind of the stent graft 200, it becomes possible to smoothly transport the stent graft 200 because it becomes difficult to apply resistance to the stent graft 200 in the process of transporting the stent graft 200.

Next, after the branch tube 220 is positioned near the entrance of the branch artery, the branch tube 220 is inserted into the branch artery. This procedure is as follows.

First, the distal end of the second transport tube 51 projecting from the sheath catheter T2 at the operator's side is inserted into the sheath catheter T2 in a folded manner.

In order to do so, in this embodiment, first, a second outer tube T3 having a bigger diameter than that of the second transport tube 51 that extends toward the operator's side is fitted over the second transport tube 51 from the distal end thereof, and then the second outer tube T3 is sent out until the distal end of the second outer tube T3 reaches near the distal end of the branch tube 220, as shown in FIG. 23. Then, the distal end of the second transport tube 51 is folded and inserted into the second outer tube T3 from a proximal end of the second outer tube T3 and then the second transport tube 51 is sent out.

With this procedure, the distal end of the second transport tube 51 projects from the distal end of the second outer tube T3, as shown in FIG. 24.

The second transport rube 51 may be folded and inserted directly into the inside of the sheath catheter T2 without providing the second outer tube T3, however, there might be a case that the folded second transport tube 51 gets stuck in the middle of the blood vessel and is difficult to proceed if the second outer tube T3 is not provided. By contrast, if the second outer tube T3 is inserted beforehand and the folded second transport tube 51 is sent forward in the second outer tube T3, it is possible to prevent the above-mentioned problem before it happens.

On the one hand, a separately provided holding device 8 is inserted into the branch artery from the distal end side of the branch artery. The holding device 8 comprises a thin-diameter holding tube 81 and a holding wire 82 that is inserted into the inside of the holding tube 81 in a state of being able to make a back and forth movement, and a ring is formed on a distal end of the holding wire 82.

Then, the holding device 8 is sent out so as to project a ring 82a arranged at the distal end of the holding device 8 from the branch artery and the ring 82a is positioned in the aorta.

With this state kept, the second transport tube 51 is operated so as to insert the distal end part of the second transport tube 51 into the ring 82a, as shown in FIG. 25. The distal end part of the second transport tube 51 is made not of a tube but is a flexible line member whose diameter is smaller than that of the tube in order to facilitate insertion of the second transport tube 51 into the ring 82a.

Next, as shown in FIG. 26, the holding tube 81 is sent out so as to bring the distal end ring 82a into the inside of the holding tube 81 and then the distal end part of the second transport tube 51 is grasped by narrowing the distal end ring 82a. At this time, as shown in FIG. 27, the second outer tube T3 is pulled out by the operator.

Next, as shown in FIG. 28, the holding member 8 is pulled toward the operator's side and the distal end part of the second transport tube 51 grasped by the holding member 8 is taken out from the body. If the second transport tube 51 is further pulled, as shown in FIG. 29, the branch tube 220 mounted on the second transport tube 51 is also pulled and inserted into and positioned at the branch artery.

As mentioned, after the main tube 210 is placed at the arch aorta and the branch tube 220 is placed at the branch artery, the main tube 210 and the branch tube 220 are expanded. A procedure to expand them is as follows.

First, regarding the main tube 210, the first control wire 212 that extends out of the body is pulled out from the operator's side of the sheath catheter T2. Then, as shown in FIG. 30, as described above with reference to FIG. 17, binding of the first binding string 211 is disconnected so that the main tube 210 is in the expanded state and attaches to the inside of the aorta.

On the other hand, regarding the branch tube 220, as shown in FIG. 13, at the operator's side part of the second transport tube 51 pulled out of the body from the branch artery, the control wire pulling-out string 62 that extends out of the control wire pulling-out window 61 is pulled so as to draw out the operator's side (the proximal end part) of the second control wire 222 from the second transport tube 51. Then, the second control wire 222 is pulled out. With this procedure, the binding of the second binding string 221 is disconnected, as shown in FIG. 14 and FIG. 30, so that the branch tube 220 is in the expanded state and attaches to the inside of the aorta.

Finally, only the stent graft 200 is left and the tubular body 41 and the second transport tube 51 are pulled out from the body. A procedure is as follows.

First, regarding the main tube 210, the first engaging wire 422 that extends out of the body from the operator's side of the sheath catheter T2 is pulled. With this procedure, as shown in FIG. 31, the first detachable string 423 is released from the tubular body 41 so that the connection of the tubular body 41 and the main tube 210 is released. Later, the tubular body 41 (and the first outer tube T1) is pulled out from the body.

On the other hand, regarding the branch tube 220, as shown in FIG. 13, at the operator's side part of the second transport tube 51 pulled out of the body from the branch artery, the engaging wire pulling string 72 that extends out of the engaging wire pulling-out window 71 is pulled so as to draw out the operator's side of the second transport tube 521 from the second transport tube 51. Then, as shown in FIG. 14, the second engaging wire 521 is pulled out. With this procedure, the binding of the second detachable string 523 is disconnected from the second transport tube 51, as shown in FIG. 15 and FIG. 31, so that the connection between the second transport tube 51 and the branch tube 220 is released. Then, the second transport tube 51 is pulled out from the body through the branch aorta.

With this procedure, as shown in FIG. 32, the stent graft 200 is indwelled at the desired position.

The present claimed invention is not limited to the above-mentioned embodiment.

For example, if the engaging wire pulling-out string and the control wire pulling-out string are made to have different shapes, respectively, it is possible for the operator to further reduce a possibility of confusing them and mistaking an order of pulling the strings. To make the strings to have different shapes means to make a color, length, or thickness different respectively in a degree capable of determining the string visually or by touch.

In addition, as shown in FIG. 33 and FIG. 34, one or a plurality of second posture control members 413 may be fixed to the first transport tube 412 intermittently by adhesive or the like in a manner of being unable to be rotated.

The second posture control member 413 is short (at least shorter than or equal to one fifth of the length of the main tube 210), and is shaped as, for example, a flat plate shape that is unable to be rotated around the axis of the contracted stent graft 200 (the main tube 210). A through bore is provided at a center of the second posture control member 413, and the first transport tube 412 and the guide wire 3 are inserted into and past the through bore. In this embodiment, the second posture control member 413 is a flat plate shape whose front end part and rear end part are tapered and whose diameters of both end parts are generally the same as the diameter of the first transport tube 412. The reason why both ends of the second posture control member 413 are tapered is to prevent the second posture control member 413 from getting caught unexpectedly by the blood vessel or another member in case of pulling out the second posture control member 413 after the stent graft 200 is indwelled.

In the above-mentioned embodiment, only the distal end part of the stent graft 200 is mounted on the posture control member 41 in a manner of being unable to be rotated around the axis so that torsion might be generated at the center part and the proximal end part of the stent graft 200, however, if the second posture control member 413 is provided also at the center part of the first transport tube 412, it is possible to reduce the torsion.

In addition, the through bore of the second posture control member 413 may be curved or bent, and the second control member 412 also may be provided with the self-alignment function. In this case, the posture control member 411 may be omitted.

The first transport tube 412 is so configured that the inner tube 412a projects from the distal end of the outer tube 412b and the proximal end part of the first transport tube 412 is high in rigidity and the distal end part thereof is low in rigidity (flexible) in the above-mentioned embodiment, however, a single tube may be used. In this case, the rigidity in the distal end part may be made different from that in the proximal end part by changing a material or a knitting of a fiber.

The first mounting mechanism that mounts the stent graft 200 on the first transport tube 412 may be as shown in FIG. 35.

More specifically, as shown in FIG. 35, the stent graft 200 is mounted on the first transport tube 412 by inserting the first engaging wire 422 into a part where the first string insertion hole 424 formed on the stent graft 200 is overlapped with the ring of the first detachable string 423 mounted on the first transport tube 412. Then, when the first engaging wire 422 is pulled out, the engaged state of the first string insertion hole 424 and the first detachable string 423 is released so that the stent graft 200 is in a state of being able to be released from the first transport tube 412.

A plurality of (four) the first string insertion holes 424 and a plurality of (four) the first detachable strings 423 are provided (in order to avoid complicating the drawings, only two of them are drawn in FIG. 35), and a number of the first engaging wires 422 corresponds to the number of the first string insertion holes 424 and the number of the first detachable strings 423.

In accordance with this arrangement, it becomes easier to release the engagement.

In addition, as shown in FIG. 36, the posture control member 411 may have an arrangement wherein two or more straight through bores 411*c* whose direction differ each other are provided in series.

Furthermore, instead of the first and second binding strings, for example, a rectangle sheet or a mesh sheet (a binding sheet) may be made to be tubular and the tubular sheet is mounted over the stent graft and keeps the stent graft in the contracted state. In this case, a control wire linearly sews an overlapped part of both end edge parts of the tubular binding sheet in order to prevent the binding sheet from being loose.

In addition, this invention is not limited to the stent graft having a single branch tube and a stent graft having two or more branch tubes may produce the same effect as that of the stent graft having one branch tube.

In addition, this invention is not limited to the above-mentioned embodiment such as the shape of the posture control member or the shape of the second control member, and various modifications can be made without departing from a scope of a spirit of this invention.

LIST OF REFERENCE CHARACTERS

200 stent graft
210 main tube
220 branch tube
100 stent graft transport device
3 guide wire
T1 first outer tube
T2 sheath catheter
T3 second outer tube
21 first expansion mechanism
211 first binding string
212 first control wire
22 second expansion mechanism
221 second binding string
222 second control wire (contracted state keeping wire)
4 main transport mechanism
41 tubular body
411 posture control member
411*a* header
411*b* mounting body
411*c* through bore
412 first transport tube
412*a* inner tube
412*b* outer tube
42 first mounting mechanism
421 first window
422 first engaging wire
423 first detachable string
424 first string insertion hole
5 auxiliary transport mechanism
51 second transport tube (transport tube)
52 second mounting mechanism
521 second engaging wire (mounted state keeping wire)
522 second window
523 second detachable string
524 second string insertion hole
6 control wire pulling-out mechanism (contracted state keeping wire pulling-out mechanism)
61 control wire pulling-out window (contracted state keeping wire pulling-out window)
62 control wire pulling-out string (contracted state keeping wire pulling-out string)
7 engaging wire pulling-out mechanism (mounted state keeping wire pulling-out mechanism)
71 engaging wire pulling-out window (mounted state keeping wire pulling-out window)
72 engaging wire pulling-out string (mounted state keeping wire pulling-out string)
8 holding device
81 holding tube

The invention claimed is:

1. A stent graft transport device comprising: a transport tube to transport a stent graft; and a mounting mechanism to mount the stent graft on the transport tube, wherein the mounting mechanism comprises a mounted state keeping wire that keeps the stent graft in a mounted state on the transport tube, and the transport tube is configured to separate from the stent graft by pulling an operation end part of the mounted state keeping wire, the operation end part of the mounted state keeping wire is housed inside of the transport tube, a mounted state keeping wire pulling-out mechanism to draw the operation end part out of the transport tube comprises a mounted state keeping wire pulling-out string, one end part of which is mounted on the mounted state keeping wire and the other end part of which is pulled out from a mounted state keeping wire pulling-out window arranged on a side peripheral surface of the transport tube, throughout an operator end section of the transport tube, which is an end section of the transport tube including the mounted state keeping wire pulling-out window and an operator end of the transport tube, the mounted state keeping wire is housed entirely inside of the transport tube, and the mounted state keeping wire pulling-out window is formed by a hole provided in the side peripheral surface of the transport tube, and a vicinity directly around the mounted state keeping wire pulling-out window is free of protrusions.

2. The stent graft transport device described in claim 1, wherein
the stent graft comprises a main tube and a branch tube bifurcated from the main tube, and the stent graft transport device is applied to the branch tube.

3. The stent graft transport device described in claim 1, the stent graft transport device being configured to transport the stent graft to a lesion part along a guide wire inserted into a blood vessel, the stent graft transport device further comprising:
a posture control member that is provided with a through bore through which the guide wire slidably passes in a curved state in one direction, wherein
the posture control member is shorter than the stent graft and mounted on a distal end part of the stent graft.

4. The stent graft transport device described in claim 3, wherein
the posture control member comprises a header and a mounting body that is arranged continuously to a rear end part of the header,
the distal end part of the stent graft is mounted on the mounting body, and
a cross sectional shape of the mounting body is noncircular.

5. A stent graft transport device comprising: a transport tube to transport a stent graft; and a contraction mechanism to contract the stent graft, wherein the contraction mechanism comprises a contracted state keeping wire that keeps the stent graft in a contracted state, and the stent graft is configured to transition from the contracted state to an expanded state by pulling an operation end part of the contracted state keeping wire, the operation end part of the contracted state keeping wire is housed inside of the transport tube, and a contracted state keeping wire pulling-out mechanism to draw the operation end part out of the transport tube comprises a contracted state keeping wire pulling-out string, one end part of which is mounted on the contracted state keeping wire and the other end part of which is pulled out from a contracted state keeping wire pulling-out window arranged on a side peripheral surface of the transport tube, throughout an operator end section of the transport tube, which is an end section of the transport tube including the contracted state keeping wire pulling-out window and an operator end of the transport tube, the contracted state keeping wire is housed entirely inside of the transport tube, and the contracted state keeping wire pulling-out window is formed by a hole provided in the side peripheral surface of the transport tube, and a vicinity directly around the contracted state keeping wire pulling-out window is free of protrusions.

6. The stent graft transport device described in claim 5, wherein
the stent graft comprises a main tube and a branch tube bifurcated from the main tube, and the stent graft transport device is applied to the branch tube.

7. The stent graft transport device described in claim 5, the stent graft transport device being configured to transport the stent graft to a lesion part along a guide wire inserted into a blood vessel, the stent graft transport device further comprising:
a posture control member that is provided with a through bore through which the guide wire slidably passes in a curved state in one direction, wherein
the posture control member is shorter than the stent graft and mounted on a distal end part of the stent graft.

8. The stent graft transport device described in claim 7, wherein
the posture control member comprises a header and a mounting body that is arranged continuously to a rear end part of the header,
the distal end part of the stent graft is mounted on the mounting body, and
a cross sectional shape of the mounting body is noncircular.

9. A stent graft transport device comprising: a transport tube to transport a stent graft; a mounting mechanism to mount the stent graft on the transport tube, and a contraction mechanism to contract the stent graft, wherein the mounting mechanism comprises a mounted state keeping wire that keeps the stent graft in a mounted state on the transport tube, and the transport tube is configured to separate from the stent graft by pulling an operation end part of the mounted state keeping wire, the operation end part of the mounted state keeping wire is housed inside of the transport tube, a mounted state keeping wire pulling-out mechanism to draw the operation end part out of the transport tube comprises a mounted state keeping wire pulling-out string, one end part of which is mounted on the mounted state keeping wire and the other end part of which is pulled out from a mounted state keeping wire pulling-out window arranged on a side peripheral surface of the transport tube, the contraction mechanism comprises a contracted state keeping wire that keeps the stent graft in a contracted state, and the stent graft is configured to transition from the contracted state to an expanded state by drawing an operation end part of the contracted state keeping wire, which is housed inside of the transport tube, out of the transport tube, and a contracted state keeping wire pulling-out mechanism to draw the operation end part out of the transport tube comprises a contracted state keeping wire pulling-out string, one end part of which is mounted on the contracted state keeping wire and the other end part of which is pulled out from a contracted state keeping wire pulling-out window arranged on a side peripheral surface of the transport tube.

10. The stent graft transport device described in claim 9, wherein the mounted state keeping wire pulling-out window and the contracted state keeping wire pulling-out window deviate from each other in an axial direction of the transport tube.

* * * * *